United States Patent
Orphanos et al.

(10) Patent No.: US 11,903,839 B2
(45) Date of Patent: *Feb. 20, 2024

(54) BASEPLATE OF A MODULAR SHOULDER JOINT PROSTHESIS AND RELATED METHODS FOR IMPLANTING THE SAME

(71) Applicant: DePuy Ireland Unlimited Company, Ringaskiddy (IE)

(72) Inventors: Stephen J. Orphanos, Bridgewater, MA (US); Brian Otrando, Cumberland, RI (US); William Murphy, Brockton, MA (US); Steven Reppucci, Lakeville, MA (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 578 days.

This patent is subject to a terminal disclaimer.

(21) Appl. No.: 17/036,706

(22) Filed: Sep. 29, 2020

(65) Prior Publication Data

US 2021/0007857 A1 Jan. 14, 2021

Related U.S. Application Data

(63) Continuation of application No. 16/044,473, filed on Jul. 24, 2018, now Pat. No. 10,813,769.

(51) Int. Cl.
*A61F 2/40* (2006.01)

(52) U.S. Cl.
CPC .......... *A61F 2/4014* (2013.01); *A61F 2/4081* (2013.01); *A61F 2002/4018* (2013.01)

(58) Field of Classification Search
CPC ... A61F 2002/4029–2002/4096; A61F 2/4014; A61F 2/40; A61F 2002/4011;
(Continued)

(56) References Cited

U.S. PATENT DOCUMENTS

| 4,045,825 A | 9/1977 | Stroot |
| 4,045,826 A | 9/1977 | Stroot |

(Continued)

FOREIGN PATENT DOCUMENTS

| WO | 2013086440 A1 | 6/2013 |

OTHER PUBLICATIONS

U.S. Appl. No. 16/044,473, filed Jul. 24, 2018, Baseplate of a Modular Shoulder Joint Prosthesis and Related Methods for Implanting the Same.

(Continued)

*Primary Examiner* — Alvin J Stewart

(57) ABSTRACT

Shoulder joint implants are disclosed herein for use in shoulder reconstruction that are configured to facilitate the inclusion a central bone screw for augmented bone fixation. The implant can include a baseplate (or metaglene) configured to secure a glenosphere or other prosthetic component to the glenoid. To facilitate lateral or proximal insertion of a central bone screw through the implant, a throughbore defined along the central axis of the metaglene can be widened to accommodate the maximum diameter of the screw. To enable fixation of the glenosphere to the metaglene, a collet can be configured to engage the smaller diameter of a glenosphere coupling element and inserted into the central throughbore. The collet and the bone screw can be separate parts, thereby making insertion of the bone screw optional. Alternatively, the collet and bone screw can be integrated together to form a unitary construct.

23 Claims, 19 Drawing Sheets

(58) Field of Classification Search
CPC ............ A61F 2002/4018; A61F 2/4003; A61F 2/3609; A61F 2002/30484

See application file for complete search history.

(56) References Cited

U.S. PATENT DOCUMENTS

| | | | |
|---|---|---|---|
| 5,314,479 A | 5/1994 | Rockwood, Jr. et al. | |
| 5,358,526 A | 10/1994 | Tornier | |
| 5,376,126 A * | 12/1994 | Lin | A61F 2/3601 623/23.11 |
| 5,728,161 A | 3/1998 | Camino et al. | |
| 5,782,920 A | 7/1998 | Colleran | |
| 5,876,459 A | 3/1999 | Powell | |
| 5,906,644 A * | 5/1999 | Powell | A61F 2/367 623/20.15 |
| 5,961,555 A | 10/1999 | Huebner | |
| 6,005,018 A | 12/1999 | Cicierega et al. | |
| 6,033,439 A | 3/2000 | Camino et al. | |
| 6,102,953 A | 8/2000 | Huebner | |
| 6,129,764 A | 10/2000 | Servidio | |
| 6,168,627 B1 | 1/2001 | Huebner | |
| 6,168,628 B1 | 1/2001 | Huebner | |
| 6,171,342 B1 | 1/2001 | Michael | |
| 6,193,758 B1 | 2/2001 | Huebner | |
| 6,508,840 B1 | 1/2003 | Rockwood, Jr. et al. | |
| 6,589,281 B2 | 7/2003 | Hyde, Jr. | |
| 6,592,622 B1 * | 7/2003 | Ferguson | A61F 2/389 623/13.12 |
| 6,620,197 B2 | 9/2003 | Maroney et al. | |
| 6,723,129 B2 | 4/2004 | Dwyer et al. | |
| 6,736,851 B2 | 5/2004 | Maroney et al. | |
| 6,783,549 B1 | 8/2004 | Stone et al. | |
| 6,863,690 B2 | 3/2005 | Ball et al. | |
| 6,953,478 B2 | 10/2005 | Bouttens et al. | |
| 6,969,406 B2 | 11/2005 | Tornier | |
| 6,984,248 B2 | 1/2006 | Hyde, Jr. | |
| 6,986,790 B2 | 1/2006 | Ball et al. | |
| 7,011,686 B2 | 3/2006 | Ball et al. | |
| 7,044,973 B2 | 5/2006 | Rockwood, Jr. et al. | |
| 7,169,184 B2 * | 1/2007 | Dalla Pria | A61F 2/4081 623/19.12 |
| 7,175,664 B1 * | 2/2007 | Lakin | A61F 2/36 623/19.14 |
| 7,198,642 B2 * | 4/2007 | Hazebrouck | A61F 2/4684 606/62 |
| 7,297,163 B2 | 11/2007 | Huebner | |
| 7,338,498 B2 | 3/2008 | Long et al. | |
| 7,527,631 B2 | 5/2009 | Maroney et al. | |
| 7,608,109 B2 | 10/2009 | Dalla Pria | |
| 7,611,539 B2 | 11/2009 | Bouttens et al. | |
| 7,615,080 B2 | 11/2009 | Ondrla | |
| 7,753,959 B2 | 7/2010 | Berelsman et al. | |
| 7,854,768 B2 | 12/2010 | Wiley et al. | |
| 7,918,892 B2 | 4/2011 | Huebner | |
| 8,002,838 B2 | 8/2011 | Klotz | |
| 8,070,755 B2 | 12/2011 | Maroney et al. | |
| 8,070,820 B2 | 12/2011 | Winslow et al. | |
| 8,118,868 B2 * | 2/2012 | May | A61F 2/367 623/13.14 |
| 8,182,542 B2 * | 5/2012 | Ferko | A61F 2/3877 623/19.13 |
| 8,192,497 B2 | 6/2012 | Ondrla | |
| 8,273,093 B2 | 9/2012 | Klotz et al. | |
| 8,303,665 B2 | 11/2012 | Tornier et al. | |
| 8,419,798 B2 | 4/2013 | Ondrla et al. | |
| 8,425,614 B2 | 4/2013 | Winslow et al. | |
| 8,460,390 B2 * | 6/2013 | Biss | A61F 2/4014 623/22.46 |
| 8,469,999 B2 * | 6/2013 | Gonzalez-Hernandez | A61B 17/80 606/232 |
| 8,579,984 B2 * | 11/2013 | Borowsky | A61F 2/4684 623/19.14 |
| 8,591,592 B2 | 11/2013 | Dreyfuss | |
| 8,632,597 B2 | 1/2014 | Lappin | |
| 8,689,425 B2 | 4/2014 | Mutchler et al. | |
| 8,702,762 B2 | 4/2014 | Jacene et al. | |
| 8,814,943 B2 | 8/2014 | Long et al. | |
| 8,920,508 B2 * | 12/2014 | Iannotti | A61F 2/30749 623/23.44 |
| 8,940,054 B2 | 1/2015 | Wiley et al. | |
| 8,945,138 B2 * | 2/2015 | Klotz | A61F 2/4684 606/99 |
| 8,968,410 B2 * | 3/2015 | Veronesi | A61F 2/4081 623/19.13 |
| 8,979,940 B2 * | 3/2015 | Porter | A61F 2/367 623/23.15 |
| 9,044,330 B2 | 6/2015 | Chavarria et al. | |
| 9,084,680 B2 * | 7/2015 | Katrana | A61F 2/4059 |
| 9,107,758 B2 | 8/2015 | Long et al. | |
| 9,283,075 B2 | 3/2016 | Wiley et al. | |
| 9,345,580 B2 * | 5/2016 | Porter | A61F 2/0811 |
| 9,351,743 B2 | 5/2016 | Kehres et al. | |
| 9,421,105 B2 | 8/2016 | Metcalfe et al. | |
| 9,421,106 B2 | 8/2016 | Splieth et al. | |
| 9,433,508 B2 | 9/2016 | Phipps | |
| 9,445,911 B2 | 9/2016 | Long et al. | |
| 9,498,344 B2 * | 11/2016 | Hodorek | A61B 17/17 |
| 9,597,190 B2 | 3/2017 | Chavarria et al. | |
| 9,610,165 B2 | 4/2017 | Poncet et al. | |
| 9,629,724 B2 | 4/2017 | Lappin | |
| 9,629,725 B2 * | 4/2017 | Gargac | A61F 2/4081 |
| 9,668,873 B2 | 6/2017 | Winslow et al. | |
| 9,763,798 B2 | 9/2017 | Chavarria et al. | |
| 9,770,334 B2 | 9/2017 | Wiley et al. | |
| 10,064,734 B2 | 9/2018 | Burkhead, Jr. et al. | |
| 10,251,744 B2 * | 4/2019 | Treacy | A61B 17/842 |
| 10,383,735 B2 | 8/2019 | Wiley et al. | |
| 10,390,972 B2 * | 8/2019 | Rao | A61F 2/4014 |
| 10,799,335 B2 * | 10/2020 | Treacy | A61B 17/842 |
| 10,813,769 B2 * | 10/2020 | Orphanos | A61F 2/4014 |
| 11,432,935 B2 * | 9/2022 | Paterson | A61F 2/30734 |
| 11,458,019 B2 * | 10/2022 | Cleveland | A61F 2/30749 |
| 2002/0004685 A1 * | 1/2002 | White | A61F 2/36 623/23.15 |
| 2003/0139818 A1 | 7/2003 | Rogers et al. | |
| 2003/0149485 A1 | 8/2003 | Tornier | |
| 2004/0193278 A1 | 9/2004 | Maroney et al. | |
| 2004/0220673 A1 * | 11/2004 | Pria | A61F 2/4081 623/19.12 |
| 2005/0004679 A1 * | 1/2005 | Sederholm | A61F 2/36 623/22.46 |
| 2005/0033443 A1 | 2/2005 | Blatter et al. | |
| 2005/0251263 A1 * | 11/2005 | Forrer | A61F 2/4014 623/19.13 |
| 2006/0142872 A1 * | 6/2006 | Klotz | A61F 2/4603 623/22.46 |
| 2007/0100458 A1 | 5/2007 | Dalla Pria | |
| 2007/0112430 A1 | 5/2007 | Simmen et al. | |
| 2007/0288020 A1 * | 12/2007 | Yang | A61F 2/0811 606/279 |
| 2008/0208348 A1 | 8/2008 | Fitz | |
| 2008/0269894 A1 * | 10/2008 | Melvin | A61F 2/0811 623/13.14 |
| 2008/0281428 A1 * | 11/2008 | Meyers | A61F 2/3607 623/20.35 |
| 2008/0294268 A1 | 11/2008 | Baum et al. | |
| 2009/0171462 A1 | 7/2009 | Poncet et al. | |
| 2009/0192621 A1 | 7/2009 | Winslow et al. | |
| 2009/0254188 A1 | 10/2009 | Maroney et al. | |
| 2010/0161066 A1 | 6/2010 | Iannotti et al. | |
| 2011/0009973 A1 * | 1/2011 | Meyers | A61F 2/389 623/18.11 |
| 2011/0054625 A1 * | 3/2011 | Ferko | A61F 2/389 623/20.14 |
| 2011/0106267 A1 | 5/2011 | Grant | |
| 2011/0130840 A1 * | 6/2011 | Oskouei | A61F 2/4059 623/18.11 |
| 2011/0224799 A1 * | 9/2011 | Stone | A61F 2/30739 623/23.26 |
| 2012/0239051 A1 | 9/2012 | de Wilde et al. | |
| 2012/0253467 A1 | 10/2012 | Frankle | |

(56) References Cited

U.S. PATENT DOCUMENTS

| | | | |
|---|---|---|---|
| 2013/0030540 A1* | 1/2013 | Leibinger | A61F 2/28 29/505 |
| 2013/0066433 A1* | 3/2013 | Veronesi | A61F 2/4081 623/19.13 |
| 2013/0090736 A1* | 4/2013 | Katrana | A61F 2/4059 623/19.13 |
| 2013/0150972 A1 | 6/2013 | Iannotti et al. | |
| 2013/0150973 A1 | 6/2013 | Splieth et al. | |
| 2013/0261751 A1 | 10/2013 | Lappin | |
| 2013/0338780 A1 | 12/2013 | Berchoux et al. | |
| 2015/0335440 A1 | 11/2015 | Linares et al. | |
| 2016/0008138 A1* | 1/2016 | Katrana | A61F 2/4014 623/19.14 |
| 2016/0030180 A1 | 2/2016 | Wecker et al. | |
| 2016/0100835 A1* | 4/2016 | Linder | A61B 17/07292 606/220 |
| 2016/0270922 A1 | 9/2016 | Pressacco et al. | |
| 2017/0042690 A1 | 2/2017 | Burkhead, Jr. et al. | |
| 2017/0079803 A1 | 3/2017 | Lang | |
| 2017/0100251 A1 | 4/2017 | Ek et al. | |
| 2017/0156847 A1* | 6/2017 | Ricci | A61B 17/1146 |
| 2017/0172751 A1 | 6/2017 | Poncet et al. | |
| 2017/0181860 A1 | 6/2017 | Nerot et al. | |
| 2017/0273800 A1 | 9/2017 | Emerick et al. | |
| 2017/0354508 A1 | 12/2017 | Chavarria et al. | |
| 2018/0021150 A1 | 1/2018 | Harper et al. | |
| 2018/0161169 A1* | 6/2018 | Cardon | A61F 2/4081 |
| 2018/0214261 A1* | 8/2018 | Treacy | A61B 17/842 |
| 2018/0303551 A1* | 10/2018 | Hopkins | G09B 23/32 |
| 2019/0046326 A1* | 2/2019 | Ball | B33Y 80/00 |
| 2020/0030108 A1* | 1/2020 | Orphanos | A61F 2/4014 |
| 2020/0085563 A1* | 3/2020 | D'Agostino | A61F 2/30734 |
| 2020/0405491 A1* | 12/2020 | Cleveland | A61F 2/30749 |
| 2021/0007857 A1* | 1/2021 | Orphanos | A61F 2/4081 |
| 2021/0128201 A1* | 5/2021 | Samuel | A61B 17/7037 |
| 2021/0251768 A1* | 8/2021 | Nelson | A61F 2/4014 |
| 2022/0008206 A1* | 1/2022 | LaReau | A61F 2/3601 |
| 2022/0265434 A1* | 8/2022 | Hodorek | A61F 2/4014 |
| 2022/0362025 A1* | 11/2022 | Cleveland | A61F 2/4081 |
| 2022/0362030 A1* | 11/2022 | Patkar | A61F 2/4014 |
| 2023/0000526 A1* | 1/2023 | Follini | A61B 17/7032 |
| 2023/0000636 A1* | 1/2023 | Dalla Pria | A61F 2/4081 |

OTHER PUBLICATIONS

[No. Author Listed] Delta Xtend, Reverse Shoulder System—Surgical Technique, DePuy Synthes, 2017 (66 pages).

Extended European Search Report for EP Application No. 19188150.7 dated Oct. 23, 2019 (8 pages).

India Examination Report for Application No. 201914027853, dated Sep. 22, 2022 (6 pages).

* cited by examiner

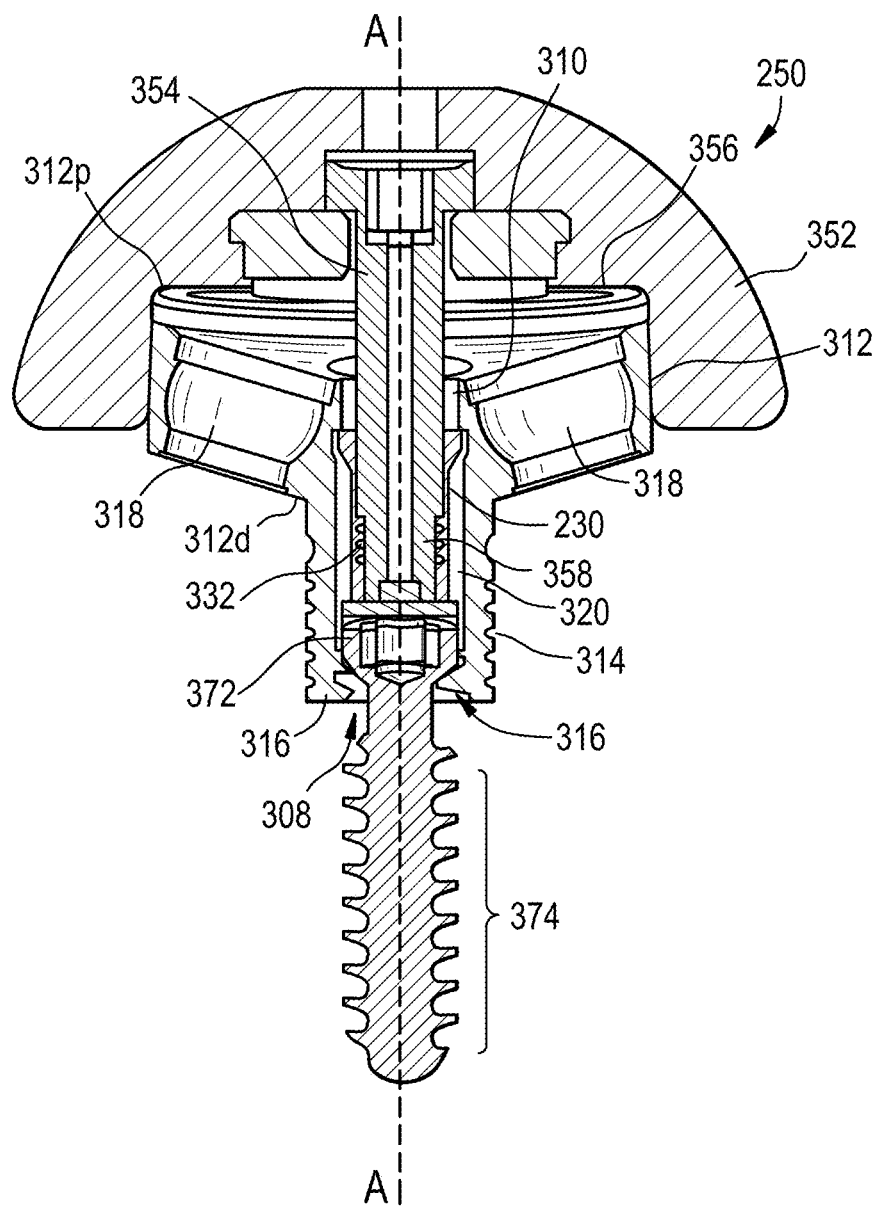

BASEPLATE OF A MODULAR SHOULDER JOINT PROSTHESIS AND RELATED METHODS FOR IMPLANTING THE SAME

CROSS REFERENCE TO RELATED APPLICATION

The present application is a continuation of and claims priority to U.S. patent application Ser. No. 16/044,473, filed Jul. 24, 2018, and entitled "Baseplate of a Modular Shoulder Joint Prosthesis and Related Methods for Implanting the Same," the contents of which is hereby incorporated by reference herein in its entirety.

FIELD

The present disclosure relates generally to orthopedic implants, and more particularly to a baseplate of a modular shoulder joint prosthesis and related methods of implanting the baseplate into a patient's scapula.

BACKGROUND

During the lifetime of a patient, it may be necessary to perform a total shoulder replacement procedure on the patient as a result of disease or trauma, for example. In a total shoulder replacement procedure, a humeral prosthesis is used to replace the natural head of the patient's humerus. The humeral prosthesis typically includes an elongated post component that is implanted into the intramedullary canal of the patient's humerus and a hemispherically-shaped prosthetic head component that is secured to the post component. In such a total shoulder replacement procedure, the natural glenoid surface of the scapula is resurfaced or otherwise replaced with a glenoid component that provides a bearing surface upon which the prosthetic head component of the humeral prosthesis articulates.

However, in some cases the patient's natural shoulder, including its soft tissue, has degenerated to a severe degree of joint instability and pain. In many such cases, it can be necessary to change the mechanics of the shoulder. Reverse shoulder implants can be used to do so. As its name suggests, a reverse shoulder implant reverses the anatomy, or structure, of the healthy shoulder. In particular, a reverse shoulder implant is designed such that the prosthetic head (i.e., the "ball" in the ball-and-socket joint), known as a glenosphere component, is secured to the patient's scapula, with the corresponding concave bearing (i.e., the "socket" in the ball-and-socket joint), known as a humeral cup, being secured to the patient's humerus. Such a reverse configuration allows the patient's deltoid muscle, which is one of the larger and stronger shoulder muscles, to raise the arm.

To secure the glenosphere component to the patient's scapula, a baseplate, sometimes referred to as a metaglene component, can be implanted onto the glenoid of the patient's scapula. For example, as shown in FIGS. 1A and 1B, a shoulder joint implant includes a metaglene component 60 that includes a platform 62 having a post 64 extending outwardly from its distal surface 66. The post 64 has a bore 68 formed about a central axis A-A of the metaglene component 60 and is configured to engage a locking screw or other coupling element protruding from a distal surface of a glenosphere component (not shown). The bore 68 extends through the entire length of the post 64. The post 64 of the metaglene component 60 is designed to be implanted into a void formed in a glenoid surface 28. Bone screws 80 can be positioned in some or all of the screw holes or apertures 74 and driven into, or otherwise secured to, the bone tissue of a patient's scapula 30, thereby fixing the metaglene component 60 in place.

In some challenging clinical situations, such as poor bone quality or anatomic limitations, it can be useful to drive a bone screw into the glenoid through the central bore 68 of the metaglene component 60. However, when the proximal width or diameter of the bore 68 is smaller than the width or diameter of the head of the screw, the surgeon may be prevented from inserting the screw through the bore using a top-down or lateral approach (i.e., distally inserting the screw from the proximal end of the metaglene component), thereby increasing the complexity of the surgical procedure. Although the proximal diameter of the bore 68 can be widened to accommodate the screw diameter, such widening can cause backward incompatibility with glenoid/glenosphere components having coupling elements with narrower widths.

Accordingly, there is a need for improved metaglene components that, for example, facilitate use of a central screw, and related methods for implanting the various embodiments of a metaglene component provided for herein, or otherwise derivable from the present disclosures, in a scapula of a patient with (or without) a central screw in a manner that maintains backward compatibility with standard glenoid/glenosphere components.

SUMMARY

The present disclosure is generally related to shoulder joint implants, and represents improvements over existing designs of such implants. These implants are often used in reverse shoulder procedures. Typically the shoulder joint implant includes a baseplate, sometimes referred to herein as a metaglene component (or metaglene). The base plate that is configured to secure a glenosphere component (or glenosphere) to the bony anatomy of the glenoid to complete the repair. As discussed in greater detail below, other components that can engage with the baseplate and/or the glenosphere component can include a collet and/or a bone screw, and in some such instances the collet and bone screw can form a singular component of the implant. The provided for embodiments can allow for backwards compatibility amongst the components of the implant, and also allow for surgeons to select a variety of different configuration types for the implant based, at least in part, on the needs and anatomy of the patient and the preferences of the particular surgeon. For example, some configurations that include a collet can allow a bone screw to be omitted from the implant, while some other configurations that include a collet and bone screw coupled together in a single, unitary component can reduce the number of steps performed during a procedure, thereby simplifying the procedure.

In one exemplary embodiment of a shoulder joint implant, the implant includes a first prosthetic component, a baseplate, and a removable collet. The first prosthetic component includes a coupling element that protrudes from a distal bearing surface of the prosthetic component. The baseplate is configured to secure the first prosthetic component to bone, and includes a post that protrudes from a distal bearing surface of the baseplate. The post defines a throughbore that extends along a proximal-distal axis of the post. The removable collet is disposed within the throughbore, and is configured to engage the coupling element of the first prosthetic component such that the first prosthetic component is fixedly coupled to the baseplate.

In some embodiments, the first prosthetic component is a glenosphere component having an integrated locking screw protruding from a distal bearing surface of the glenosphere component. The collet can be dimensioned to engage the coupling element, with the coupling element having a diameter that is less than a diameter of the throughbore of the baseplate. Additionally, or alternatively, the collet can include a plurality of proximally-extending arms that are radially compressible to facilitate at least one of insertion and removal of the collet in the throughbore of the baseplate. One or more of the proximally-extending arms can include a lateral protrusion that is configured to engage an annular recessed portion of an inner sidewall of the throughbore when the arms are not compressed, which in turn can fix the removable collet in place with respect to the first prosthetic component and/or with respect to the baseplate itself at a predetermined depth in the throughbore of the baseplate. Further, one or more of the proximally-extending arms can have a proximal ramped bearing surface that is configured to bear against a counterpart bearing surface of a prosthetic implant tool. The arm(s) can be radially compressed in response to the counterpart bearing surface of the prosthetic implant tool bearing against the proximal ramped bearing surface, thus disengaging the lateral protrusion of the arm(s) from the recessed portion of the inner sidewall of the throughbore. This radial compression feature can be used to facilitate insertion and/or removal of the collet within the throughbore of the baseplate.

In some embodiments, the collet can include one or more keys protruding from one or more of the arms of the collet. The keys of the collet can configured to engage with one or more keyways defined longitudinally along an inner sidewall of the throughbore of the baseplate to align and guide the collet into the baseplate. The keys of the collet can be configured to engage with the keyways defined along the inner sidewall of the throughbore to resist rotation of the collet while disposed within the throughbore of the baseplate. The keys of the collet can be configured to engage with the keyways along the inner sidewall of the throughbore to form a locking mechanism that provides a torsional resistive force that counteracts a torque imparted by the coupling element of the first prosthetic component while screwing the coupling element into the collet to form a taper lock between the first prosthetic component and the baseplate or while unscrewing the coupling element out of the collet to break the taper lock between the first prosthetic component and the baseplate. The length of the keyways can define a distal most depth at which the removable collet can be seated in the throughbore of the baseplate. In some embodiments, the distance between the annular recessed portion and the distal most depth of the keyways can be a predefined distance that is greater than the height of the collet such that the collet bottoms out at the distal end of the one or more keyways while the coupling element of the glenosphere component is unscrewed from the collet.

In some embodiments, the implant can include a bone screw that has a proximal head and a distal threaded portion. In such embodiments, the throughbore of the baseplate can be dimensioned to facilitate insertion of the bone screw that has a diameter that is greater than a diameter of the coupling element of the first prosthetic component. Further, in some such embodiments, the collet can be dimensioned to engage the coupling element, with the coupling element having a diameter that is less than a diameter of the central bone screw. In some instances, the collet and the central bone screw can be separate components. This can result, for example, in a configuration in which the collet is disposed within the throughbore of the baseplate, proximal to the proximal head of the central bone screw. In some such embodiments, the collet can be disposed within the throughbore of the baseplate after the central bone screw is laterally inserted into the throughbore. In some embodiments, the implant can be devoid of a central bone screw.

In instances in which the implant includes a central bone screw that has a proximal head and a distal threaded portion, the collet can be coupled to the proximal head of the central bone screw. Alternatively, or additionally, the proximal head of the central bone screw can include a shoulder portion that is of a spherical and/or conical shape, and an inner sidewall of the throughbore at the distal end of the post can include a threaded sidewall portion that is configured to support the shoulder portion of the central bone screw. In some embodiments that include a central bone screw that has a proximal head and a distal threaded portion, the distal threaded portion of the central bone screw can extend through an opening at the distal end of the post, being configured to secure the baseplate to bone.

One exemplary method of implanting a shoulder prosthetic implant in a scapula of a patient includes reaming a glenoid of a scapula such that a surface of the glenoid is complementary to a distal bearing surface of a baseplate of a prosthetic shoulder implant, drilling a hole into the glenoid to receive a post that protrudes from the distal bearing surface of the baseplate, and disposing the post of the baseplate into the glenoid through the drilled hole. The method further includes securing a plurality of peripheral bone screws into the glenoid through one or more screw holes defined in the baseplate, and laterally inserting a removable collet into a throughbore defined in the baseplate. The throughbore extends along a proximal-distal axis of the baseplate of the post. Still further, the method includes securing a first prosthetic component of the prosthetic shoulder implant onto a proximal bearing surface of the baseplate such that a coupling element protruding from a distal bearing surface of the first prosthetic component is secured to the collet within the throughbore of the baseplate.

The method can further include laterally inserting a central bone screw through the throughbore of the baseplate prior to inserting the removable collet, and securing a distal threaded portion of the central bone screw into the glenoid through an opening at the distal end of the post of the baseplate. The collet can be coupled to a proximal head of a central bone screw and the method can further include laterally inserting the collet and the central bone screw together into the throughbore of the baseplate, and securing a distal threaded portion of the central bone screw into the glenoid through an opening at the distal end of the post of the baseplate.

The throughbore of the baseplate can be dimensioned to facilitate insertion of a central bone screw having a diameter that is greater than a diameter of the coupling element of the first prosthetic component. Further, the collet can be dimensioned to engage the coupling element of the first prosthetic component having a diameter that is less than a diameter of the central bone screw. In some embodiments, the first prosthetic component is a glenosphere component having an integrated locking screw protruding from a distal bearing surface of the glenosphere component.

The removable collet can include a plurality of compressible arms. In some such embodiments, the method can include removing the collet from within the throughbore of the baseplate using a tool by laterally inserting the tool into the throughbore of the baseplate, and rotating a distal end of the tool to engage the threaded portion of the plurality of arms. The method can further include continuing to rotate the distal head until the distal head radially compresses the plurality of arms away from a recessed sidewall portion of the throughbore, and proximally pulling the collet out of the throughbore.

BRIEF DESCRIPTION OF THE DRAWINGS

The accompanying drawings, which are incorporated herein and constitute part of this specification, illustrate exemplary embodiments, and together with the general description given above and the detailed description given below, serve to explain the features of the various embodiments:

FIG. 3 is a side, partially transparent view of the shoulder joint implant of FIG. 2B;

DETAILED DESCRIPTION

Figure 1A:
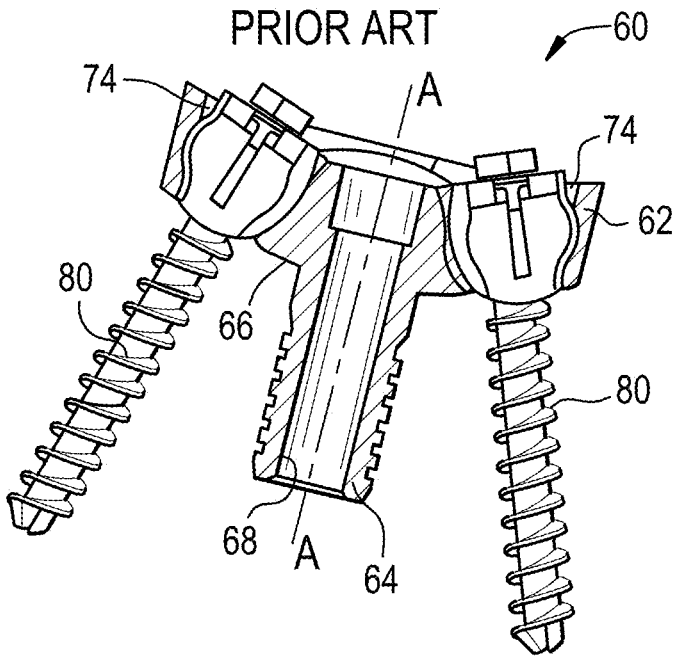
FIG. 1A is a side, partial cross-sectional view of one example of a shoulder joint implant of the prior art.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Sizes and shapes of the devices, and the components thereof, can depend on a variety of factors, including but not limited to an anatomy and tendencies of the subject (i.e., patient) in which the devices will be used, the size and shape of components with which the devices will be used, the methods and procedures in which the devices will be used, and the preferences of the surgeon operating the devices and/or otherwise performing the related procedure(s).

In the present disclosure, like-named components of the embodiments generally have similar features and/or purposes, unless stated otherwise. Additionally, a number of terms may be used throughout the disclosure interchangeably but will be understood by a person skilled in the art. Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can be easily determined for any geometric shape (e.g., references to widths and diameters being easily adaptable for circular and linear dimensions, respectively, by a person skilled in the art). Additionally, to the extent that terms are used in the disclosure to describe a direction, orientation, and/or relative position of the disclosed prosthetic devices and components thereof and/or for performing a disclosed method of assembly and/or implantation of such devices, such terms are not intended to be limiting. For example, a person skilled in the art will recognize that terms of direction, orientation, and/or relative position (e.g., proximal, distal, medial, lateral, etc.) can be used interchangeably depending, at least in part, on the perspective view of the surgeon or other operator.

The present disclosure is generally related to shoulder joint implants, and represents improvements over existing designs of such implants. These implants are often used in reverse shoulder procedures. Typically the shoulder joint implant includes a baseplate, sometimes referred to herein as a metaglene component (or metaglene). The baseplate is configured to secure a glenosphere component (or glenosphere) to the bony anatomy of the glenoid to complete the repair. As discussed in greater detail below, other components that can engage with the metaglene component and/or the glenosphere component can include a collet and/or a bone screw, and in some such instances the collet and bone screw can form a singular component of the implant. The provided for embodiments can allow for backwards compatibility amongst the components of the implant, and also allow for surgeons to select a variety of different configuration types for the implant based, at least in part, on the needs and anatomy of the patient and the preferences of the particular surgeon. For example, some configurations that include a collet can allow a bone screw to be omitted from the implant, while some other configurations that include a collet and bone screw coupled together in a single, unitary component can reduce the number of steps performed during a procedure, thereby simplifying the procedure.

Although the various embodiments disclosed herein disclose fixing a glenosphere component to the metaglene component, one of skill in the art will recognize the other prosthetic components can be coupled to the metaglene component, such as but not limited to a glenoid component configured to replace or augment the glenoid surface of the scapula. A person skilled in the art will also understand how the disclosures provided for herein can be adapted for use with devices and procedures associated with other joints without departing from the spirit of the present disclosure.

Figure 2A:
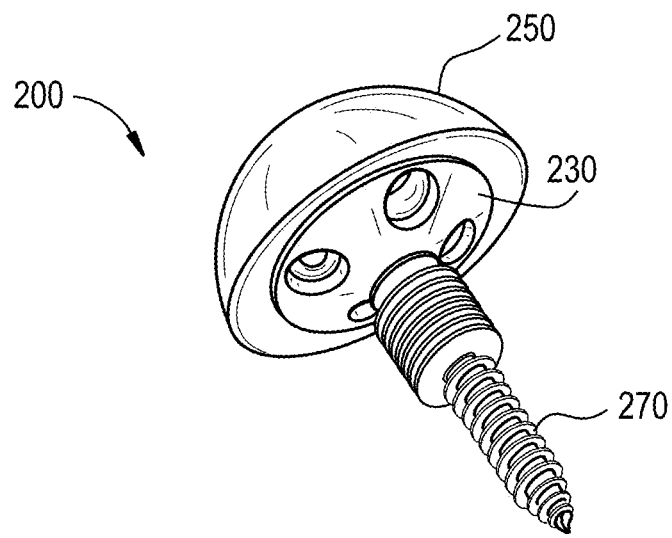
FIG. 2A is a perspective view of one exemplary embodiment of a shoulder joint implant.
Figure 2B:
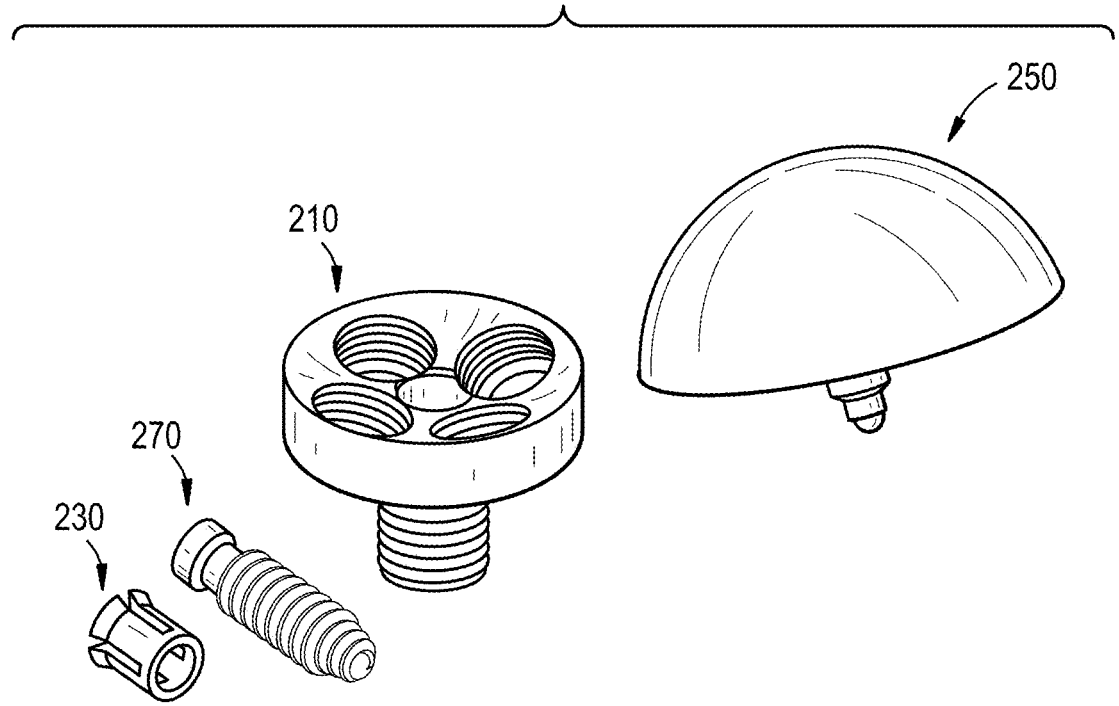
FIG. 2B is a perspective exploded view of components of the shoulder joint implant of FIG. 2A, the components including a metaglene component, a collet, a glenosphere component, and a bone screw.

FIGS. 2A, 2B, and 3 provide for one exemplary embodiment of a shoulder joint implant 200. As shown, the shoulder joint implant 200 can include a metaglene (or metaglene component) 210, a collet 230, a glenosphere (or glenosphere component) 250, and a central bone screw 270, which, as explained below, can be optional. More particularly, the collet 230 and the bone screw 270 can be disposed in a central throughbore of the metaglene 210 such that the bone screw can be driven into the glenoid and the collet can secure the glenosphere 250 to the metaglene 210. Each of these components is described in greater detail below.

Figure 4A:
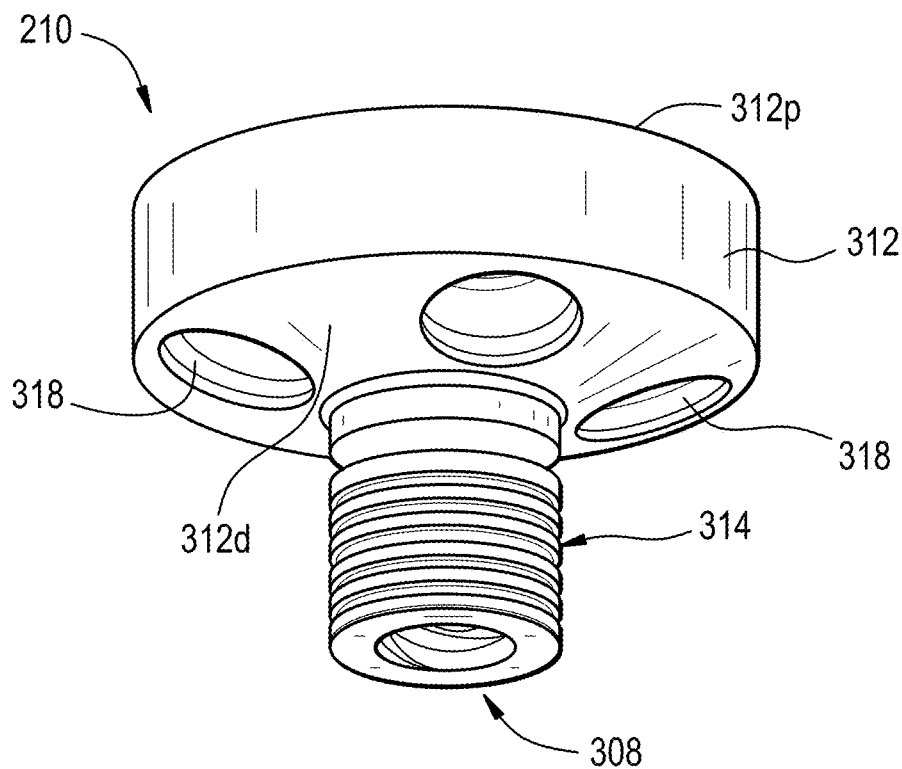
FIG. 4A is a bottom perspective view of the metaglene component of FIG. 2B.
Figure 4B:
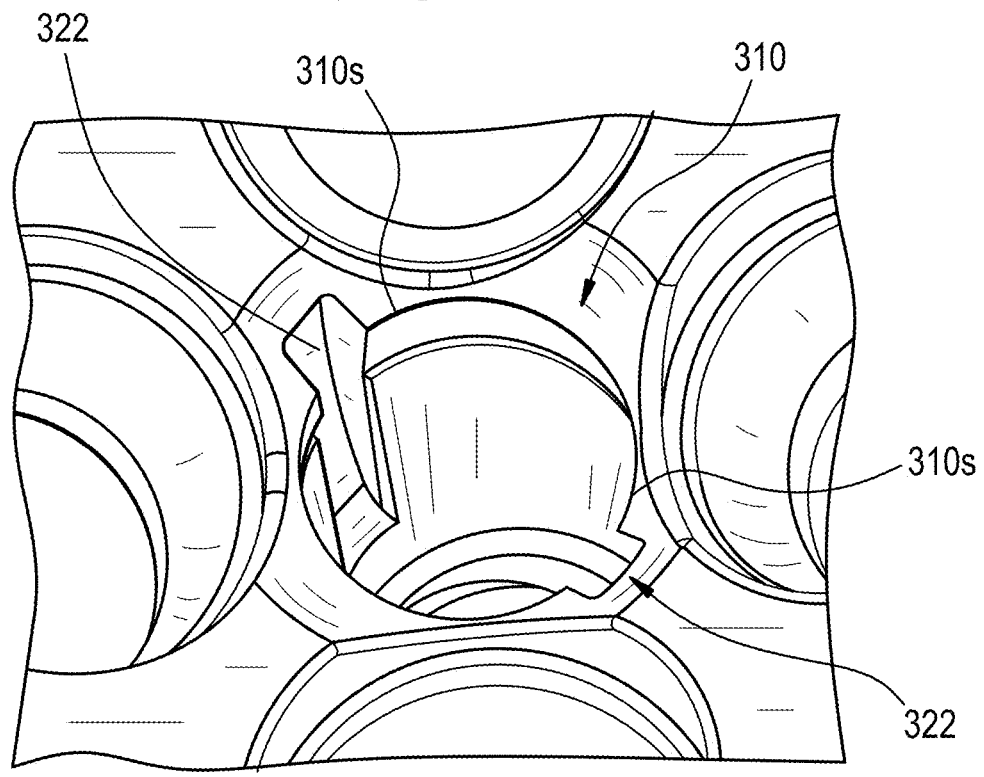
FIG. 4B is a detailed top view of the metaglene component of FIG. 4A.
Figure 4C:
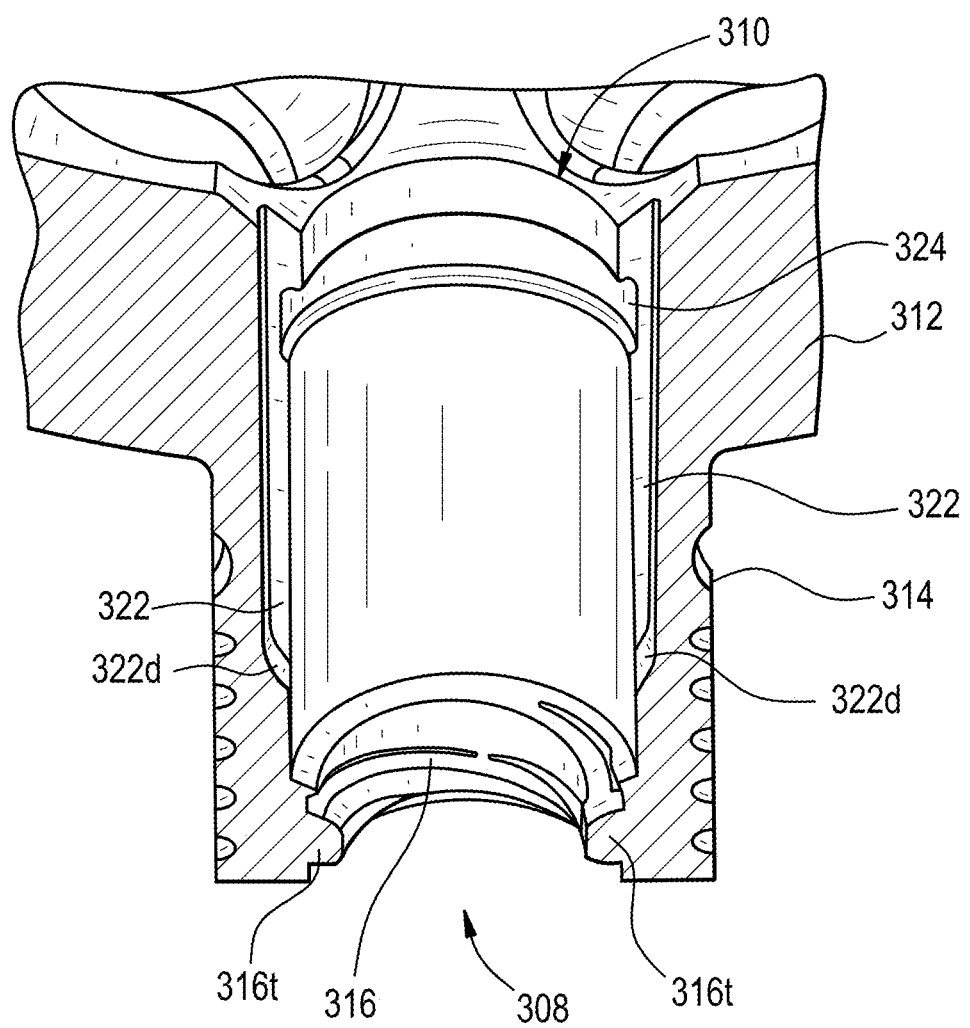
FIG. 4C is a detailed side, cross-sectional view of the metaglene component of FIG. 4B.

The metaglene 210 is one component of the shoulder joint implant 200, and is illustrated in more detail in FIGS. 4A-4C. In the illustrated embodiment, the metaglene 210 includes a platform 312 having a post 314 extending outwardly from a bottom or distal-facing surface 312*d*. The platform 312 can be generally configured such that its bottom or distal-facing surface 312*d* engages in a complementary manner with a surface of the glenoid when implanted and a top or proximal-facing surface 312*p* engages in a complementary manner with the glenosphere 250 or other prosthetic component when coupled together. More specifically, the distal-facing surface 312*d* of the platform 312 can have a convex shape configured to conform to a concave surface of the glenoid. Further, the proximal-facing surface 312*p* of the platform 312 can have a concave shape configured to be complementary with a surface it engages with of the glenosphere 250.

Figure 1B:
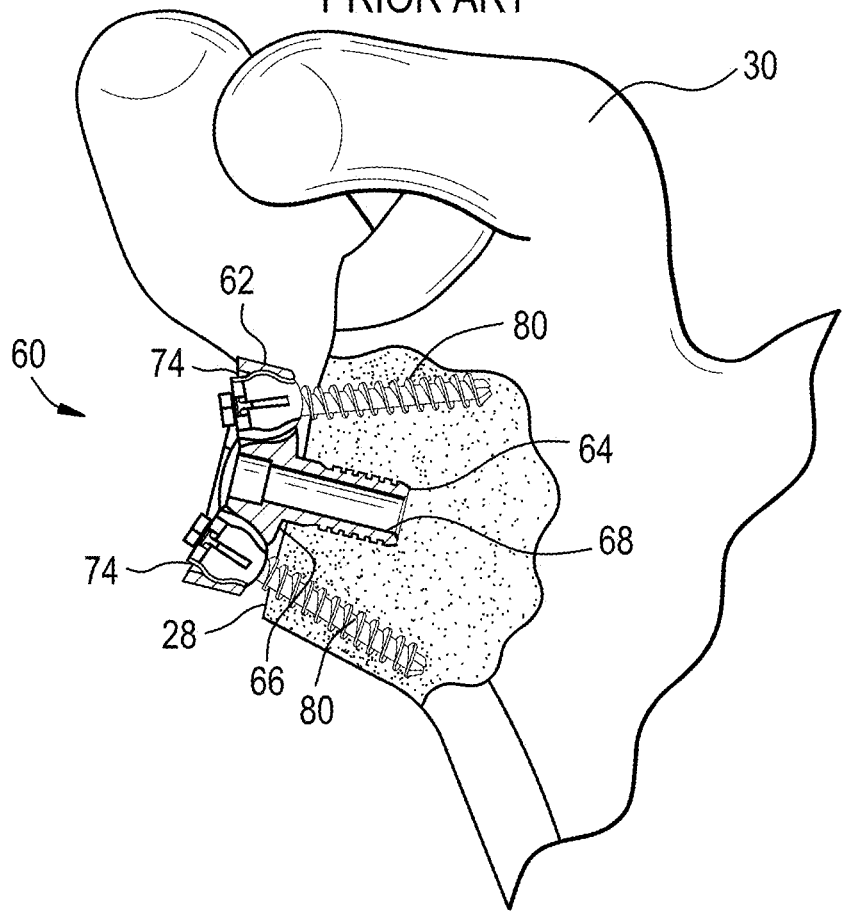
FIG. 1B is a schematic side view of the shoulder joint implant of FIG. 1A coupled to a scapula.

The platform 312 can include a central throughbore 310 extending through a thickness of the platform 312. Its configuration is described in greater detail below with respect to its relationship with the post 314 and the collet 230. Although illustrated in a central configuration, a person skilled in the art will recognize the throughbore 310 can be located in a non-central manner without departing from the spirit of the present disclosure. The platform 312 can also include one or more screw holes or apertures 318 that likewise extend through a thickness of the platform 312. The apertures 318 can be positioned in any variety of configurations, and in the illustrated embodiment there are four that are positioned radially outward from the central throughbore 310 the such that they are approximately equidistant from each other. The apertures 318 can be used to receive peripheral bone screws (not shown, but operate in a similar manner as screws 80 of FIGS. 1A and 1B) to be driven into the bony anatomy of the glenoid to help fix the metaglene 210 in place. Any number and configuration of apertures 318 can be used without departing from the spirit of the disclosure, including using no apertures.

The post 314 can generally extend distally from the distal-facing surface 312*d* of the platform 312, and can be configured to be press fit into a void or hole drilled into the glenoid of the patient's scapula, thereby providing a first form of bone fixation. In some embodiments, to further augment bone fixation, the post 314 can have a throughbore 320 extending therethrough. In the illustrated embodiment the throughbore 320 is centrally disposed such that it is formed and centered around a central axis A-A of the metaglene 210, although other locations with respect to the metaglene 210 are possible. This location also places the throughbore 320 in-line with the throughbore 310 of the platform 312. The throughbore 320 can have an inner diameter sized to accommodate a maximum diameter of a bone screw 270 (e.g., the diameter of a screw head 372). For example, as shown in the illustrated embodiment, the bone screw 270 can be inserted laterally or proximally through the throughbore 320 of the metaglene 210 such that the screw head 372 is seated on a threaded distal portion 316 of the post 314. The threaded distal portion 374 of the screw 270 exits the metaglene 210 through a distal opening 308 of the post 314. As described in more detail below with respect to FIG. 7, the threaded distal portion 316 of the post 314 can be configured to facilitate the use of smaller screws and thus avoid the need to increase the size of the post 314. A distal opening 308 of the post 314 can be used to allow a central bone screw (not shown) to exit the metaglene 210 into bone.

As shown in FIGS. 4B and 4C, the central throughbore 310 of the metaglene 210 can be configured to facilitate insertion of the collet 230 and optionally a bone screw 270. For example, in some embodiments, one or more slots or recesses, sometimes referred to herein as keyway(s) 322, can be defined longitudinally along an inner sidewall 310*s* of the throughbore 310. The keyways can be configured to slidably mate with keys 512 protruding from the collet 230, described in greater detail below, to help orient and guide insertion of the collet 230 within the throughbore 310 of the metaglene 210. The keyways 322 can extend partially along the length of the throughbore 310 and terminate at a distal stop 322*d* at which to seat the collet 230.

In some embodiments, the mating of the keys 512 and keyways 322 can provide resistance to torsional rotation, e.g., while the glenosphere 250 is screwed into or otherwise coupled to the collet 230. For example, in some embodiments, the keys 512 of the collet 230 can be configured to engage with the keyways 322 along the inner sidewall 310*s* of the throughbore 310 to form a locking mechanism that provides a torsional resistive force that counteracts a torque imparted by the locking screw of the glenosphere 250 while screwing the locking screw into the collet 230 to form a taper lock (e.g., a Morse taper lock) between the distal facing surface of the glenosphere 250 and the proximal facing surface of the baseplate 210. Likewise, the mating of the keys 512 and the keyways 322 form a locking mechanism that provides a torsional resistive force that counteracts a torque imparted by the locking screw in an opposite direction while unscrewing the coupling element out of the collet to break the taper lock between the first prosthetic component and the baseplate. As shown in the illustrated embodiment, the keyways 322 can be shaped to form rectangular or other suitably shaped slots. Although two keyways are shown in the illustrated embodiment, more or less than two keyways (e.g., four) can be defined within the throughbore 310 of the metaglene 210.

Alternatively, or additionally, in some embodiments the central throughbore 310 of the metaglene 210 can be configured to define an annular groove or recess, sometimes referred to herein as a catch 324, in the inner sidewall 310s of the central throughbore 310. As described in more detail with respect to FIG. 7, the annular catch 324 can be configured to engage the lip 514 of the collet, thereby securing the collet 230 in place at a predetermined depth.

Alternatively, or additionally, in some embodiments a threaded distal portion 316 can be defined along the inner sidewall 310s of the central throughbore 310 at the distal end of the post 314. In some embodiments, the threaded distal portion 316 of the central throughbore 310 can include two or more threads 316t configured to coarsely match the threads of a central bone screw (e.g., 270). As shown in FIG. 4C, the threads 316t of the distal threaded portion 316 can be configured at an oblique angle or otherwise radially contoured to serve as a spherical or conical bearing surface for the head of the central bone screw. As described in more detail with respect to FIG. 6A-6C, the distal threaded portion 316 of the throughbore 310 can allow the use of a central bone screw having a maximum thread size without having a large screw head, and thereby avoiding the need to increase the size of the post.

The platform 312 and post 314 can come in a variety of configurations, shapes, and sizes. As shown, the base plate 312 can be substantially cylindrical with a substantially circular cross-section. As discussed above, a top surface 312p of the platform 312 can have a concave configuration, and a bottom surface 312d of the platform can have a convex configuration. The post 314 can also be substantially cylindrical with a substantially circular cross-section, with a diameter of the post 314 being less than a diameter of the platform 312. In the illustrated configuration, the diameter of the post 314 is approximately half the size of the diameter of the platform 312, although other proportions are certainly possible, such as the diameter of the post 314 being approximately one-quarters or three-quarters the size of the diameter of the platform 312.

While the sizes of the components can certainly vary, in some exemplary embodiments a diameter of the platform 312 can be approximately in the range of about 15 millimeters to about 30 millimeters, a thickness of the platform 312 (as viewed, proximal-to-distal) can be approximately in the range of about 3.5 millimeters to about 14 millimeters, and a radius of curvature of the concavity of either or both the proximal-facing and distal-facing surfaces 312p, 312d of the platform 312 being approximately in the range of about 0.5 millimeters to about 2.0 millimeters. A person skilled in the art will recognize that a thickness of the platform 312 may change over its surface area of the radius of curvature of the concavity of the platform for its proximal-facing surface 312p is not the same as the radius of curvature of the concavity of the platform for its distal-facing surface 312d.

A diameter of the post 314 can be approximately in the range of about 5 millimeters to about 20 millimeters, and a thickness of the post 314 (as viewed, proximal-to-distal) can be approximately in the range of about 5 millimeters to about 30 millimeters. In some exemplary embodiments, a diameter of the platform 312 is approximately 22 millimeters or approximately 27 millimeters, a thickness of the platform 312 is approximately 7 millimeters, approximately 8 millimeters, or approximately 10 millimeters, a radius of curvature of the concavity of each of the proximal-facing surface 312p and the distal-facing surface 312d of the platform 312 is approximately 1.0 millimeters, a diameter of the post 314 is approximately 10 millimeters, and a thickness of the post can be approximately 13 millimeters, approximately 23 millimeters, or approximately 28 millimeters.

The glenosphere 250 is illustrated in FIGS. 2A, 2B, and 3. In some embodiments, the glenosphere 250 can include a hemispherical body 352 having a locking screw 354 or other coupling element that extends outward from a distal surface 356 of the hemispherical body 352. The distal surface 356 can be complementary in size and shape to the proximal-facing surface 312p of the metaglene 210 so that they can form a secure fit when coupled together. In the illustrated embodiment, the fit is a thread fit, but in other embodiments it could be a snap fit or any other coupling technique known to those skilled in the art for coupling two mechanical components. While many different sizes, shapes, and configurations of the glenosphere 250 are possible, in some exemplary embodiments a diameter of the hemispherical body 352 is approximately in the range of about 20 millimeters to about 80 millimeters, such as 40 millimeters, and a height of the hemispherical body 352 (as viewed, proximal-to-distal) can be approximately in the range of about 10 millimeters to about 40 millimeters, such as 20 millimeters. Likewise, in some exemplary embodiments, a diameter of the locking screw 354 can be approximately in the range of about 2.5 millimeters to about 10 millimeters, such as 5 millimeters, and a height of the locking screw 354 (as viewed, proximal-to-distal) can be approximately in the range of about 12.5 millimeters to about 50 millimeters, such as 25 millimeters.

In previous iterations of shoulder joint implants, a glenosphere locking screw was screwed directly into a central throughbore of a metaglene to secure the glenosphere to the metaglene. However, when the diameter of the central throughbore of the metaglene is widened to accommodate the diameter of the head of a bone screw, the diameter of the central throughbore can exceed the diameter or width of a glenosphere locking screw such that the locking screw cannot be screwed directly to the metaglene.

Figure 5:
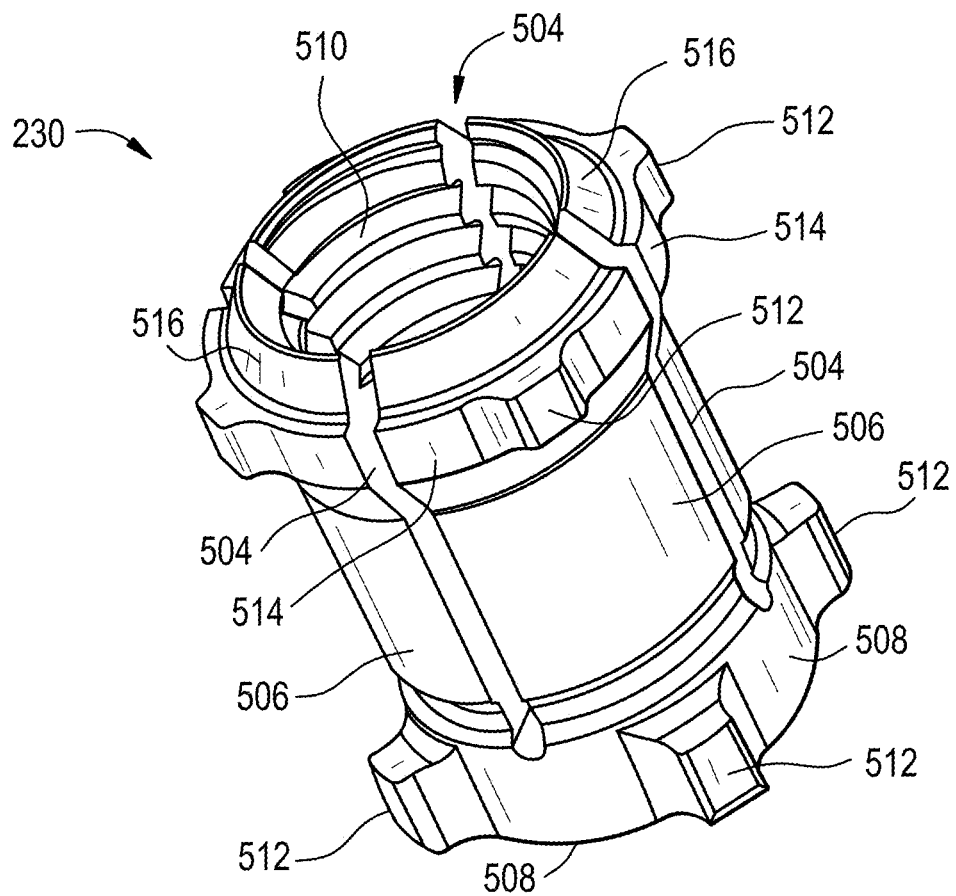
FIG. 5 is a perspective view of the collet of FIG. 2B.

To address this problem, the present disclosure provides for the collet 230, which is illustrated in FIG. 5 and sometimes referred to as an adaptor or a reducing bushing. As shown in the illustrated embodiment, the collet 230 can include a substantially hollow cylindrical body 502. The collet can also include open-ended slots 504 spaced about the circumference of the cylindrical body 502 to form radially compressible arms 506 that extend proximally from an annular base portion 508. As described in more detail below with respect to FIG. 7, the radially compressible arms of the collet 230 can be configured to facilitate insertion and/or removal of the collet by flexing in response to changes in the diameter of the throughbore 310 of the metaglene 210. In some embodiments, each of the proximally-extending arms 506 can have an inner threaded portion 510 configured to at least partially surround and threadably engage the locking screw 354 of the glenosphere 250 or other prosthetic component.

In some embodiments, the collet 230 can include one or more lateral protrusions that are configured to orient and guide the collet into the throughbore of the metaglene, sometimes referred to herein as key(s) 512. For example, as shown in the illustrated embodiment, the keys 512 can have a rectangular or other suitable shaped profile and protrude radially outward from one or more of the arms 506 and the annular base portion 508 of the collet 230. As described in more detail below with respect to FIG. 7, the keys 512 can be configured to slide along the keyways 322 formed along an inner sidewall of the throughbore 310 of the metaglene 210. When mated to the inner sidewall of the throughbore, the keys 512 can provide resistance to torsional rotation, e.g., while the glenosphere 250 is screwed into or otherwise coupled to the collet 230.

In some embodiments, the collet 230 can include an annular protrusion, sometimes referred to herein as a ridge or lip 514. As described in more detail below with respect to FIG. 7, the lip can be disposed or segmented across one or more of the arms 506 and configured to engage a catch 324 (e.g., an annular groove or recess) defined within the throughbore of the metaglene, thereby securing the collet 230 in place at a predetermined depth.

In some embodiments, the collet 230 can include a tapered or conical proximal bearing surface 516 at the proximal end of each arm 506. As described in more detail below with respect to FIGS. 12A-12C, the conical or tapered bearing surface 516 can be used to facilitate removal of the collet from within the central throughbore of the metaglene.

The collet 230 can be disposed within the central throughbore 310 to effectively reduce the inner diameter of the throughbore and threadably engage or otherwise capture the locking screw 354 of the glenosphere 250. In some embodiments, the collet 230 can have an inner threaded portion 332 that enables the glenosphere locking screw 354 to be screwed directly into the collet and thereby draw the glenosphere 250 onto the proximal-facing bearing surface 312p of the metaglene 210.

The collet 230 can be laterally or proximally inserted into the throughbore 310 of metaglene 210 until the collet 230 reaches a predetermined depth within the throughbore 310. In other words, the collet 230 is advanced distally towards and into the throughbore 310. As previously described, in some embodiments, the keyways 322 and/or the catch 324 defined in the sidewall 310s of the central throughbore 310 can be used to engage the keys 514 and/or the lip 514 of the collet 230 and thereby position the collet at a predetermined depth. Alternatively, or additionally, the collet 230 can be inserted into the throughbore of the metaglene component after the central bone screw 270 is laterally or proximally inserted into the throughbore, such the collet 230 can be disposed proximal to a head of the central bone screw 270. In some embodiments the collet 230 can be inserted into the throughbore of the metaglene component with no central bone screw 270 disposed therein.

Like the other components, the collet 230 can have a variety of sizes, shapes, and configurations. In some exemplary embodiments, the collet has a diameter approximately in the range of about 3 millimeters to about 15 millimeters, such as about 6.4 millimeters, and a height (as viewed, proximal-to-distal) approximately in the range of about 5 millimeters to about 20 millimeters, such as about 10 millimeters. Although shown as a cylindrical shape, other shapes are possible provided that the shape is complementary to the shape of the throughbore 310 of the metaglene 210 into which it is inserted.

Figure 6A:
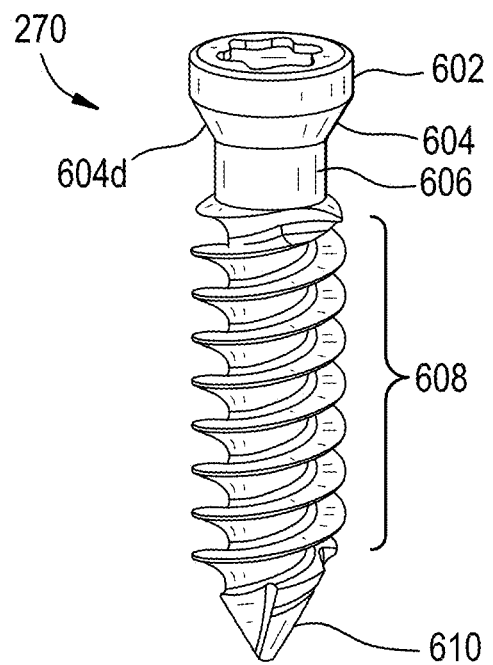
FIG. 6A is a side perspective view of the bone screw of FIG. 2B.
Figure 6B:
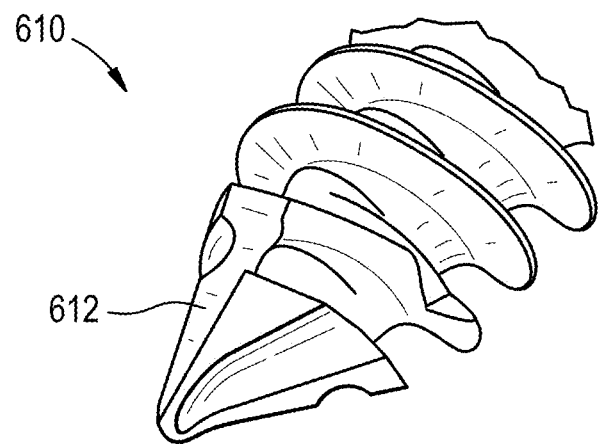
FIG. 6B is a detailed perspective view of a distal end the bone screw of FIG. 6A.
Figure 6C:
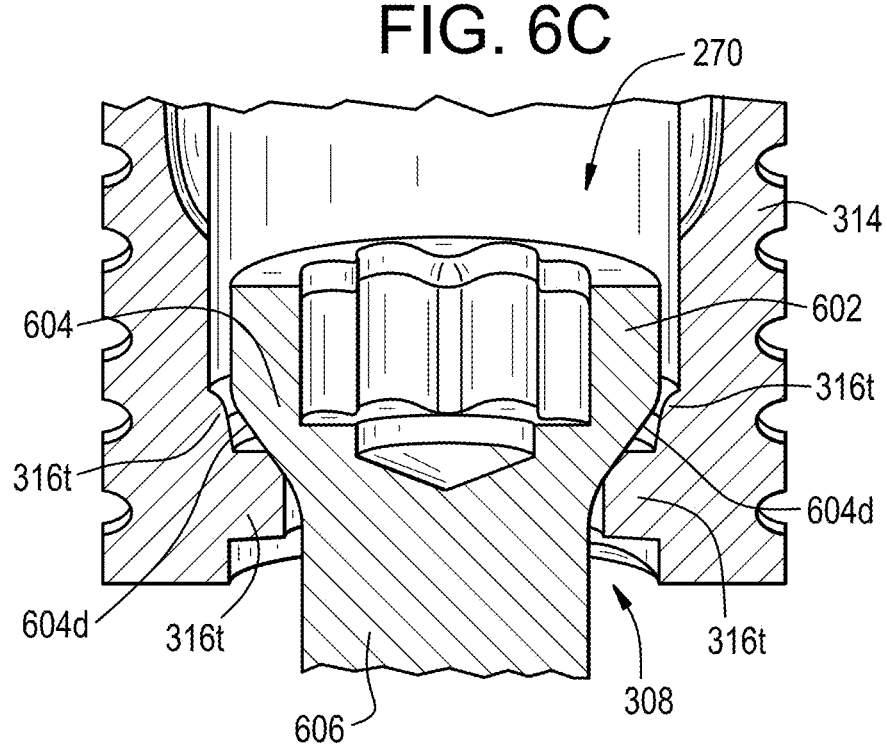
FIG. 6C is a detailed side, cross-sectional view of the metaglene component of FIG. 4C and a proximal end of the bone screw of FIG. 6A.

FIGS. 6A, 6B, and 6C illustrate a central bone screw 270 that is configured for use with the shoulder joint implant of FIG. 2A. As shown in the illustrated embodiment, the central screw 270 can have a screw head 602, a shoulder portion 604, an unthreaded neck portion 606, a distal threaded portion 608 and a distal tip 610. In some embodiments, the shoulder portion 604 can be shaped to form a spherical or conical bearing surface 604d for the screw head 602. Notably, the central bone screw 270 is an optional component that can be omitted while still allowing the rest of the shoulder joint implant 200 to be successfully used for a repair procedure.

Typical screw heads are generally much larger in diameter than the thread diameter in order to provide a sufficient bearing surface. However, in some embodiments, in view of the present disclosures, the screw head 602 can have an outer diameter that is the same or approximately the same as the maximum outer diameter of the distal threaded portion 608. In such embodiments, the spherical or conical shoulder portion 604 can serve as the bearing surface for the screw head. For example, the shoulder portion 605 of the screw can provide a spherical or conical bearing surface 604d that extends inward at an oblique angle between the head portion 602 and the neck portion 606.

Thus, as shown in the illustrated embodiment of FIG. 6C, when the screw 270 is inserted through the central throughbore 310 and seated at the distal opening 308 of the metaglene post 314, the spherical or conical bearing surface 604d of the screw can bear against the distal threaded portion 316 of the throughbore 310. For example, as shown, the threads 316t of the distal threaded portion 316 can be angled or otherwise radially contoured to match or approximately match the spherical or conical bearing surface 604d of the screw 270. Thus, the distal threaded portion 316 can serve as a proximal-facing bearing surface that substantially conforms to shaped profile of the shoulder portion 604 to support the screw head 602 within the post 314. As shown in the illustrated embodiment, the spherical or conical shoulder portion 604 can be unthreaded to prevent it from passing through the distal threaded portion 316 of the baseplate, such that the shoulder portion can serve as the bearing surface of the screw 604 to the baseplate 210. Accordingly, in some embodiments the distal threaded portion 316 of the central throughbore 310 can allow the use of a central bone screw in which the screw head and threaded portion are very close in size (e.g., diameter) and still provide a bearing surface to provide optimal compression. Additionally, the use of central bone screws having reduced diameter heads can provide an advantage in that increases in the size (e.g., outer diameter) of the metaglene post can be avoided and thus requiring removal of less bone in the glenoid.

In some embodiments, the unthreaded neck portion 606 of the bone screw 270 can be cylindrical or substantially cylindrical in shape. The unthreaded neck portion 606 can be configured to provide a clearance between the spherical or conical shoulder portion 604 to the threaded portion 608. The amount of such clearance provided by the neck portion 606 can be configured so that the distal threaded portion 608 of the screw 270 does not mate directly to the metaglene 210 when the screw head 602 is seated within the post 314.

In some embodiments, the unthreaded neck portion 606 of the screw 606 can allow a "free spinning screw" design in which the screw is disposed within the baseplate, as shown in FIG. 3. The unthreaded neck portion 606 can help prevent the distal threaded portion 608 from binding up within the post 314 of the baseplate 210. Accordingly, the unthreaded neck portion 606 allows the screw 600 to turn within the bone and thereby drag the baseplate 210 further into the bone to provide additional compression between the bone and the distal facing surface 312d of the platform 312. This feature allows the screw to act like any other socket head cap screw that is assembled into a counter-bored hole to provide compression.

In some embodiments, the unthreaded neck portion 606 can provide an additional bearing surface or contact surface area between the screw 600 and baseplate 210. Additionally, the unthreaded neck portion 606 can be spherical which allows the screw 600 to pivot off axis from the baseplate 210 and thus not influence the baseplate 210 to glenoid bone interface. In some embodiments, the unthreaded neck portion 606 can be omitted such that the screw 606 could still function as intended with less contact area.

In some embodiments, the diameter and length of the screw 270 can be varied to accommodate user needs. For example, in some embodiments, the length of the screw 270 can be approximately in the range of about 15 millimeters to about 80 millimeters, and in some embodiments it is approximately 40 millimeters. However, in some embodiments, the surgeon can be provided with a number of central bone screws having different screw lengths from which to choose depending, at least in part, on the depth of the glenoid vault in which the screw is to be secured. In some embodiments, the maximum outer diameter of the distal threaded portion 608 of the screw 270 can be approximately in the range of about 6.0 millimeters to about 6.5 millimeters. In some embodiments, the distal threaded portion 640 of the screw 270 can be configured for optimized purchase or grip within the glenoid vault and allow for single or multiple leads to aid in insertion speed. In some embodiments, the distal tip 610 of the screw 270 can include an optimized bone cutting self-tapping feature 612. The self-tapping feature 612 as shown is a channel formed in an outer surface of the distal threaded portion 640, which makes it easier to insert the screw 270 into bone.

In view of the present design, and the fact that in at least some instances a bone screw may not be needed, the surgeon can choose to not use the bone screw 270 in the assembly of the shoulder joint implant 200. If the central bone screw 270 is not used, the collet 230 can be inserted in the metaglene 210 without the bone screw. In some embodiments, the shoulder joint implant 200 can be fixedly attached to the bony anatomy of the glenoid as part of a reverse shoulder reconstruction procedure, described in more detail with respect to FIG. 9.

Figure 7:
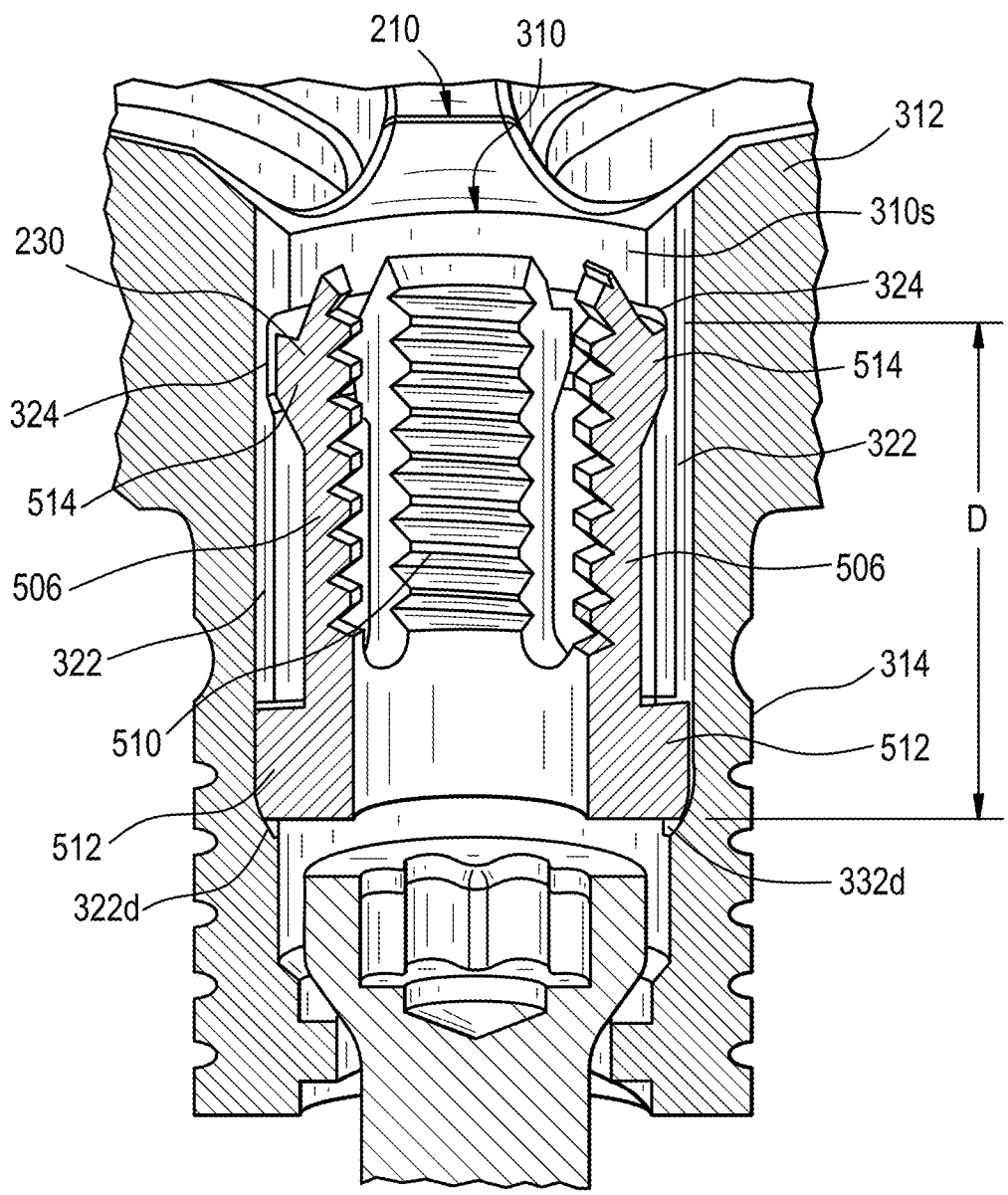
FIG. 7 is a detailed side, cross-sectional view of the metaglene component and the proximal end of the bone screw of FIG. 6A and the collet of FIG. 5.

FIG. 7 illustrates the collet 230 and bone screw 270 disposed within the central throughbore 310 of the metaglene 210. In the illustrated embodiment, the collet 230 and the bone screw 270 are separate components. Thus, the surgeon can choose whether or not to include the central bone screw 270 in the assembly of the shoulder joint implant 200. For example, in some embodiments, if the surgeon chooses to include the central bone screw in the assembly, the screw 270 can be laterally or proximally inserted through the central throughbore 310 (i.e., advanced distally towards and into the metaglene 210). Thereafter, the collet 230 can be laterally or proximally inserted into the central throughbore 310 such the collet 230 is disposed proximal to the head 602 of the screw 270. Alternatively, if the surgeon chooses not to include the central bone screw 270, the collet 230 can be laterally or proximally inserted into the central throughbore 310 without no bone screw.

A detailed description of the structure and procedure for laterally or proximally inserting and seating a central bone screw 270 within the central throughbore 310 is described above with respect to FIGS. 6A-6C and thus is omitted here for the sake of brevity.

In some embodiments, the collet 230 can be laterally or proximally inserted into the central throughbore 310 of the metaglene 210 by aligning the keys 512 of collet 230 with the keyways 322 of the throughbore 310. For example, as previously discussed with respect to FIGS. 4A-4C and 5, the collet 230 can include one or more lateral protrusions or keys 512 that are configured to slidably mate with corresponding slots or keyways 322 defined in the throughbore 310. Once the collet 230 is oriented by aligning the keys 512 with the keyways 322, the collet 230 can be pushed laterally or proximally into the central throughbore 310 such that it is guided by the keys 512 sliding laterally or proximally along the respectively keyways 322.

In some embodiments, as the collet 230 enters the throughbore 310, the inner sidewall 310s of throughbore 310 bears against the ridge or lip 514 of collet 230 and thereby causes the radially compressible arms 506 of the collet to flex inward while remaining in contact with the wall. As previously discussed with respect to FIGS. 4A-4C and 5, the lip 514 of the collet 230 can be an annular protrusion disposed across one or more of the arms 506 and configured to engage an annular groove or catch 324 defined horizontally along the inner sidewall 310s of the throughbore 310.

In some embodiments, when the lip 514 of the collet 230 reaches the location of the catch 324, the radial compression force applied by the inner sidewall 310s can release and cause the collet arms 506 to flex outward such that the lip snaps into or otherwise mates within the catch. In some embodiments, the engagement of the lip 514 of the collet 230 and the catch 324 can create an audible and/or tactile cue (e.g., a "click") to notify the surgeon that the collet has reached the desired depth. In some embodiments, the engagement of the lip 514 of the collet 230 with the catch 324 can coincide with the keys 512 at the annular base portion 508 of the collet 230 hitting a mechanical stop 322d at the bottom of the keyways 322. With the collet 230 secured at the predetermined depth, a glenosphere (e.g., the glenosphere 250) or other prosthetic component can be attached to the metaglene 210 using techniques described herein or otherwise known to those skilled in the art.

In some embodiments, the location of the mechanical stop 322d at the distal end of the keyways 322 can define a distal most depth, or the key depth, at which the distal end of the collet 230 is capable of bottoming out within the throughbore 310 of the baseplate 210. The distance D between the distal most depth of the keyways 322 and the annular recessed portion defined in the inner sidewall 310s of the throughbore 310, or catch 324, can be a predefined distance that is slightly greater than the height of the collet 230. For example, in some embodiments, the distance D between the distal most depth of the keyways and the catch 324 can be greater than the height of the collet by an amount in the range between approximately 0.5 millimeters and approximately 2.0 millimeters, such as about 1.0 millimeters. In some embodiments, where the height of the collet 230 is in the range between approximately 5 millimeters and 20 millimeters, the distance D can be in the range between approximately 4.0 millimeters and 22 millimeters. For example, in some embodiments, where the height of the collet 230 is approximately 10 millimeters, the distance D can be in the range between 9 and 12 millimeters, such as about 11 millimeters. Thus, the additional tolerance provided by the predefined distance D between the catch 324 and the distal end 322d of the keyways 322 can allow the collet 230 to be properly secured between the catch 324 and the distal end 322d of the keyways 322.

The additional tolerance provided by the predefined distance D can be useful during removal of the glenosphere (e.g., 250). For example, in some embodiments, the glenosphere and thus the glenosphere locking screw (e.g., 354) can be unscrewed (e.g., rotated counterclockwise) to remove the glenosphere from the baseplate 210. As the locking screw is unscrewed, the ridge or lip 514 of the collet 230 releases from the catch 324 in the sidewall 310s of the throughbore 310, thereby causing the collet to be pushed towards the mechanical stop 322d of the keyways 322 until the distal end of the collet 230 bottoms out against the stop. Once the collet 230 bottoms out against the mechanical stop 322d, the continuing turning of the locking screw 354 to unscrew the glenosphere (e.g. 250) causes the load to be transferred through glenosphere such that the taper lock connection between the glenosphere and the baseplate 210 is pulled apart. In some embodiments, the taper lock connection can be a Morse taper lock between the distal facing surface of the glenosphere and the proximal facing surface of the baseplate 210. This is essentially a "Jacking Screw" function for removal of the glenosphere from the baseplate.

Figure 8:
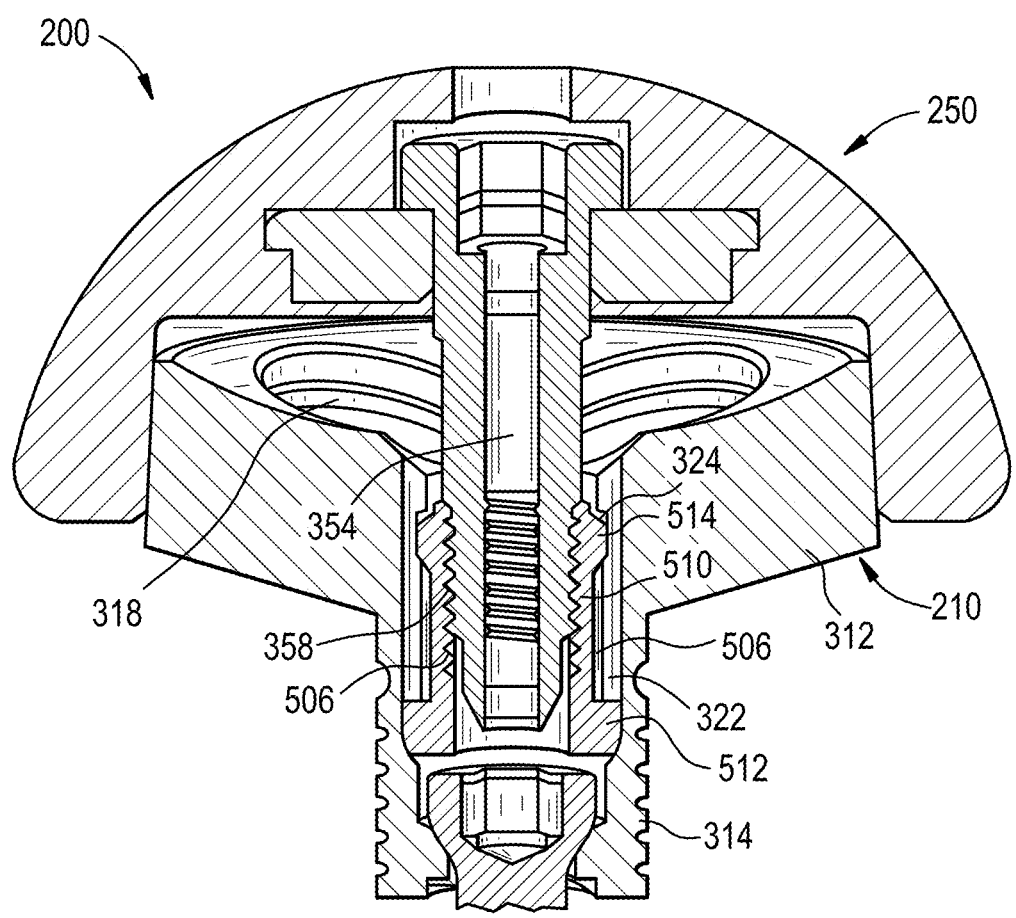
FIG. 8 is a side, cross-sectional view of the metaglene component, proximal end of the bone screw, and the collet of FIG. 7, and the glenosphere component of FIG. 2B that includes a locking screw.

FIG. 8 illustrates the shoulder joint implant 200 with the glenosphere 250 secured to the collet 230. As shown in the illustrated embodiment, the collet 230 can be disposed within the central throughbore 310 to effectively reduce the inner diameter of the throughbore 310 and threadably engage or otherwise capture the locking screw 354 of the glenosphere 250. For example, as shown, each of the proximally-extending collet arms 506 can have an inner threaded portion 510 configured to at least partially surround the locking screw 354 such that a threaded portion 358 of the locking screw 354 can be screwed into the collet 230 and thereby draw and secure the hemispherical body 352 of the glenosphere 250 onto the proximal-facing surface 312 of the metaglene 210. When the collet 230 is secured to the inner sidewall 310s of the throughbore 310, the engagement of the keys 512 and the keyways 322 can provide resistance to torsional rotation, e.g., while the glenosphere 250 is screwed into or otherwise coupled to the collet 230. Alternatively or in addition, engagement of the lip 514 of the collet 230 and the catch 324 can prevent or otherwise limit vertical displacement of the collet 230 within the throughbore 310.

In exemplary embodiments any and all of the metaglene 210, the collet 230, the glenosphere 250, and the screw 270 can be made from any number of implantable metallic materials or other biocompatible materials to form the implant. Some non-limiting examples of materials suitable for forming the various components implant can include titanium, cobalt-chrome, stainless steel, and other metals known to those skilled in the art, and some plastic materials, such as but not limited to, polyetheretherketone (PEEK) and Ultra High Molecular Weight Polyethylene (UHMWPE). In some instances, the various components (e.g., the metaglene 210, the collet 230, the glenosphere 250, and the screw 270) can be made from the same material, while in other embodiments one or more components can be made from different materials. For example, in some instances in may be beneficial to have the metaglene 210, the collet 230, and the glenosphere 250 formed from surgical grade titanium, while the screw 270 is formed from surgical grade titanium coated with a porous biocompatible material (e.g., a hydroxyapatite (HA) coating). Additionally, a person skilled in the art will recognize that a number of different material blends can be used to form any component of the implants provided for herein or otherwise derivable from the present disclosures.

Figure 9:
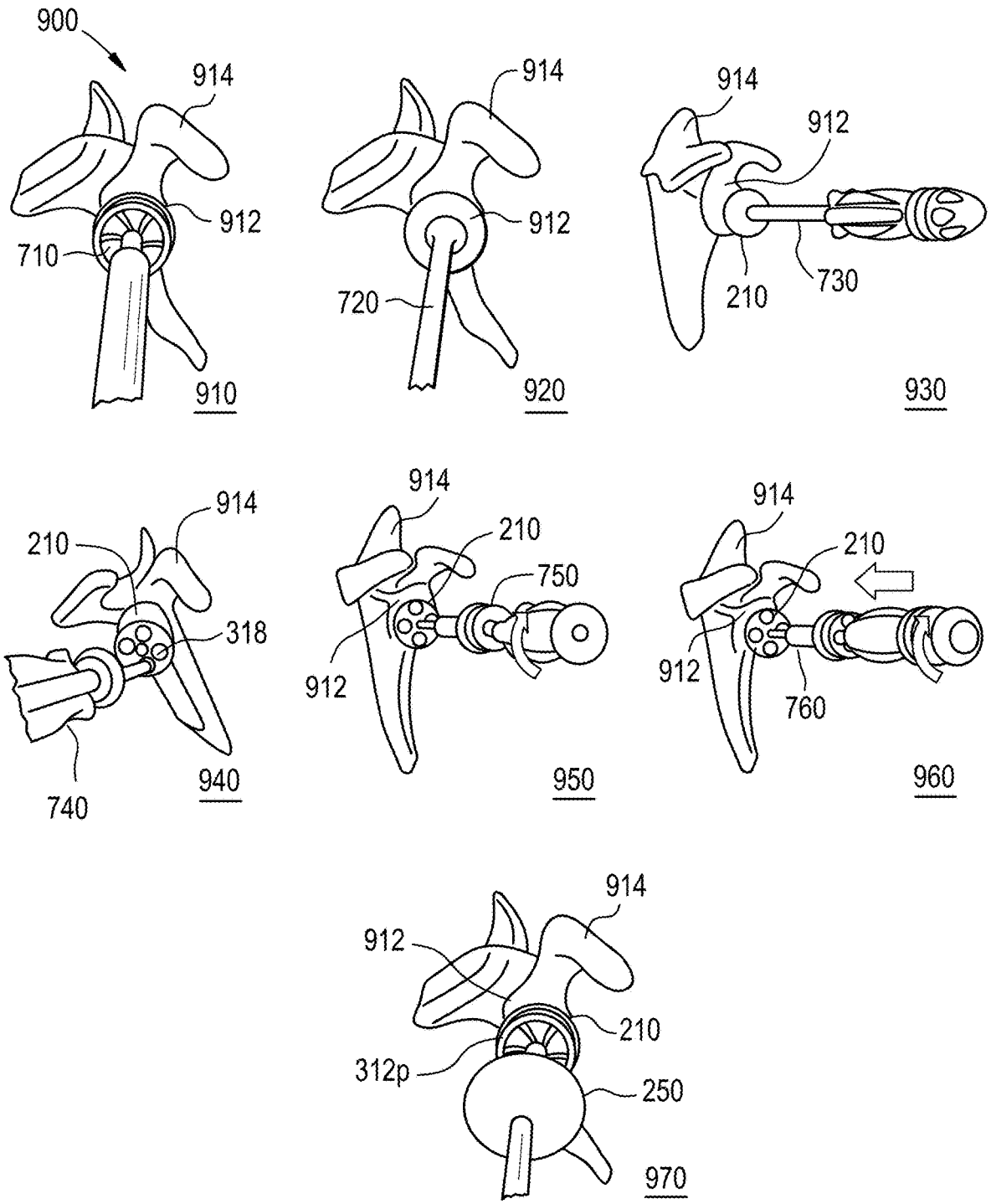
FIG. 9 is a schematic illustration of one exemplary embodiment of a method of implanting a shoulder implant like the shoulder implant of FIGS. 2A-8.

FIG. 9 illustrates an exemplary embodiment of a method 900 of implanting the shoulder joint implant 200 in a patient's scapula. In the illustrated embodiment, the shoulder joint implant 200 can be implanted as part of a reverse shoulder reconstruction surgery in which the glenosphere (i.e., the "ball" in the ball-and-socket joint) is secured to the patient's scapula. A humeral cup (i.e., the "socket" in the ball-and-socket joint) can be secured to the patient's humerus to provide a corresponding concave bearing for the glenosphere. Such a reverse configuration allows the patient's deltoid muscle, which is one of the larger and stronger shoulder muscles, to raise the arm. Although the illustrated configuration uses the implant 200 described above, at least some of the components associated with or otherwise used in conjunction with the implant 200 may not be easily visible in the various blocks 910, 920, 930, 940, 950, 960, and 970. In view of the disclosures provided for herein, and their related illustrations, a person skilled in the art will understand how the various components of the implant 200 engage the various portions of the patient's anatomy, and/or the components of the implant 200 and related tools used in conjunction with the procedures disclosed with respect to FIG. 9.

At block 910, a glenoid 912 of the patient's scapula 914 can be reamed such that a bony surface of the glenoid 912 conforms to the distal bearing surface (e.g., 312d) of the metaglene (e.g., 210). In some embodiments, a glenoid resurfacing reamer 710 can be used to prepare the glenoid 912 to have an approximately smooth, curved surface having the same or substantially the same radius of curvature as the distal-facing surface 312d of the metaglene 210. The diameters may also be complementary, whether that means the same or substantially equal, or the glenoid 912 being a little larger with the labrum (not visible in block 910) being adjacent to help keep the metaglene 210 in the desired location.

At block 920, a hole can be drilled into the glenoid 912 to receive the metaglene post (e.g., 314) of the metaglene (e.g., 210). In some embodiments, a cannulated stop drill 720 aligned with a central guide pin (not shown) can be used to drill the central hole.

At block 930, the metaglene post 314 (not visible) can be disposed into the glenoid 912 through the drilled hole. In some embodiments, a metaglene delivery instrument 730 can be secured to the metaglene 210 and used to insert the metaglene post 314 into the hole drilled into the glenoid 912. The metaglene post 314 can be slightly oversized relative to the diameter of the drilled hole to enable a press fit. Once the post 314 and the distal-facing surface 312d (not visible) of the metaglene 210 is seated on the bone 912, the metaglene delivery instrument 730 can be removed.

At block 940, one or more peripheral bone screws (not shown) can be driven into the glenoid through one or more screw apertures 318 of the metaglene 210 to secure the metaglene 210 to bone. In some embodiments, a screw driver 740 can be used to screw the peripheral bone screws at superior and/or inferior locations in the glenoid 912. In some embodiments, peripheral bone screws can be placed at lateral and/or medial locations of the glenoid.

At optional block 950, a bone screw 270 (not visible) can be laterally or proximally inserted through the central throughbore 310 (not visible) of the metaglene 210 prior to inserting the collet 230. In some embodiments, a screw driver 750 can be used to screw a distal threaded portion 608 (not visible) of the bone screw 270 into the glenoid through an opening 308 (not visible) at the distal end of the post 314 (not visible) of the metaglene 210. In some embodiments, the bone screw can be laterally or proximally inserted as previously described with respect to FIGS. 6A-6C.

At block 960, the collet 230 (not visible) can be laterally or proximally inserted into the central throughbore 310 (not visible) defined in the metaglene 210 into the post 314 (not visible). In some embodiments, a collet delivery instrument 760 can be coupled to the collet 230 (not visible) and used to push the collet 230 into the central throughbore 310 (not visible) as previously described with respect to FIG. 7.

At block 970, the glenosphere 250 of the shoulder joint implant 200 can be secured onto the proximal bearing surface 312p of the metaglene 210. For example, in some embodiments, a locking screw 354 (not visible) or other coupling element protruding from a distal bearing surface of the glenosphere 250 can be secured to the collet 230 (not visible) within the throughbore of the metaglene 210. In some embodiments, the glenosphere 250 can be screwed into or otherwise coupled the collet 230 as previously described with respect to FIG. 8.

Figure 10A:
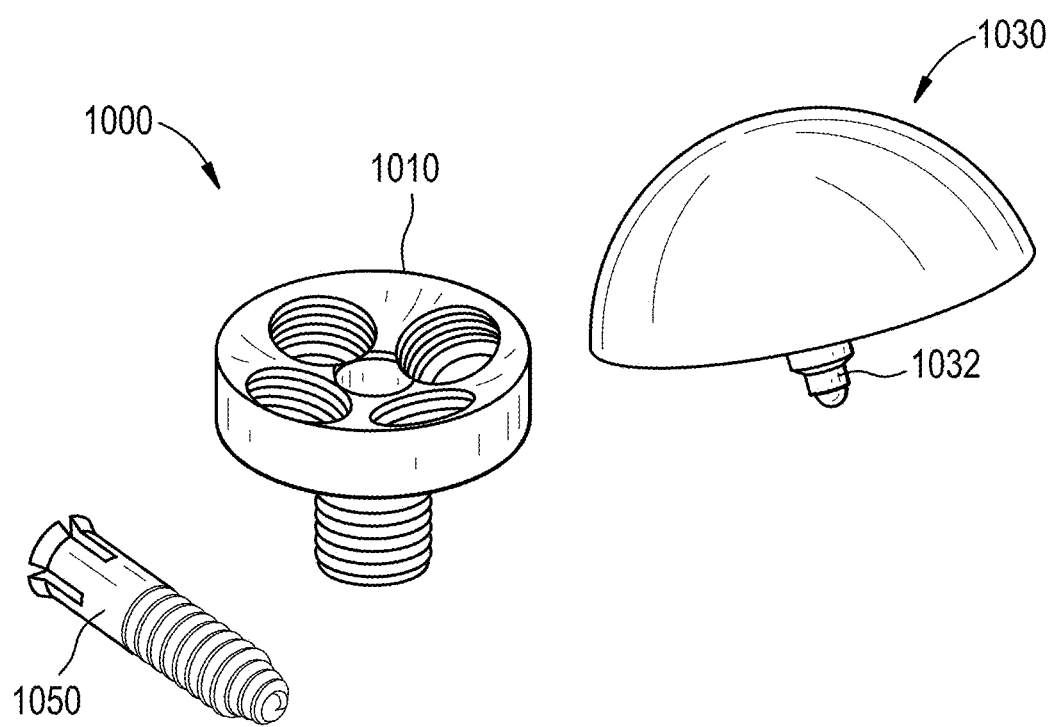
FIG. 10A is a perspective exploded view of another exemplary embodiment of a shoulder joint implant, the implant having components that include a metaglene component, a glenosphere component, and an integrated collet and bone screw.
Figure 10B:
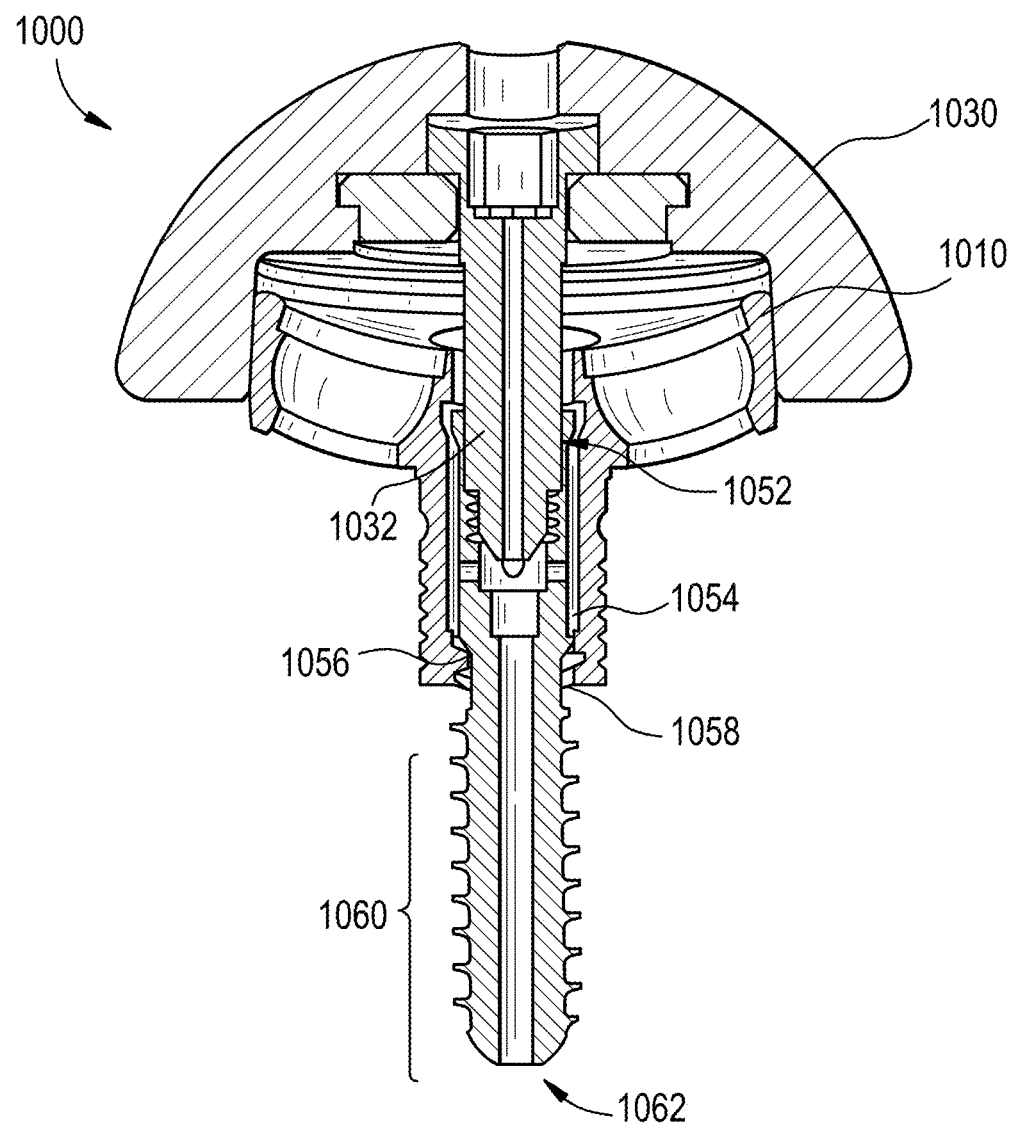
FIG. 10B is a side, partially transparent view of the shoulder joint implant of FIG. 10A.

FIGS. 10A and 10B provide for another exemplary embodiment of a shoulder joint implant 1000. As shown, the shoulder joint implant 1000 can include a metaglene 1010, a glenosphere 1030, and an integrated collet and central bone screw 1050. Accordingly, the integrated collet and central bone screw 1050 can allow surgeons to add a bone screw down the center axis of the metaglene component as a single unitary component in one step, while maintaining backwards compatibility with existing glenosphere components.

Except as described below or as will be readily appreciated by one having ordinary skill in the art, the metaglene 1010 and the glenosphere 1030 are substantially similar to the metaglene 210 and the glenosphere 250 described above with respect to FIGS. 2A-9. A detailed description of the structure and function thereof is omitted here for the sake of brevity. The shoulder joint implant 1000 can include any one or more of the features of the shoulder joint implant 200.

As shown in the illustrated embodiment, the integrated collet and bone screw 1050 can include a collet portion 1052, a proximal screw head 1054, a spherical or conical shoulder portion 1056, an unthreaded neck portion 1058, a distal threaded portion 1060, and a distal tip 1062. Except as described below or as will be readily appreciated by one having ordinary skill in the art, the shoulder portion 1056, an unthreaded neck portion 1058, a distal threaded portion 1060, and a distal tip 610 are substantially similar to the spherical or conical shoulder portion 604, the unthreaded neck portion 606, the distal threaded portion 608, and the distal tip 610 of the screw 270 described above with respect to FIGS. 6A-6C. A detailed description of the structure and function thereof is omitted here for the sake of brevity.

In some embodiments, the collet portion 1052 can be fixedly coupled to the proximal head 1054 of the screw to form the integrated collet and central bone screw 1050. For example, the collet portion 1052 can mechanically attached, welded, bonded, or attached in any other manner of ways to the proximal screw head 1054. Alternatively, the collet portion 1052 can be integrally formed on the proximal screw head 1054, e.g., using a three dimensional (3D) printing technique.

Figure 10C:
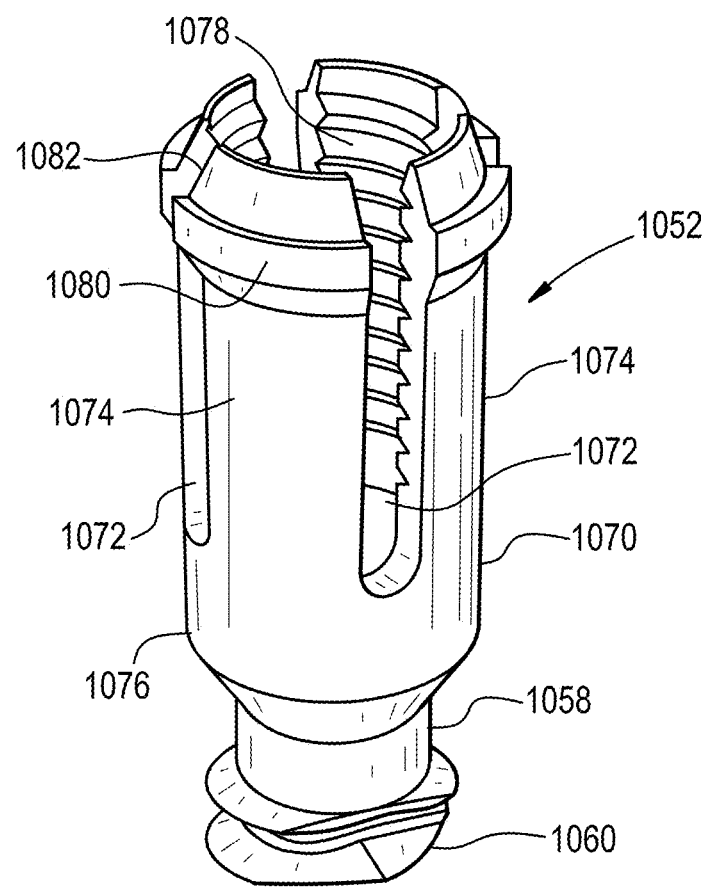
FIG. 10C is a detailed perspective view of the integrated collet and bone screw of FIG. 10A.

As shown in the illustrated embodiment of FIG. 10C, the collet portion 1052 can have a substantially hollow cylindrical body 1070. The collet portion 1052 can include open-ended slots 1072 spaced about the circumference of the cylindrical body 1070 to form radially compressible arms 1074 that extend proximally from an annular base portion 1076. The radially compressible arms 1074 of the collet portion 1052 can be configured to facilitate insertion and/or removal of the collet by flexing in response to changes in the diameter of the throughbore of the metaglene 1010.

In some embodiments, each of the proximally-extending arms 1074 can have an inner threaded portion 1078 configured to at least partially surround and threadably engage a locking screw 1032 of the glenosphere 1030 or other prosthetic component. In some embodiments, the collet portion 1052 can include an annular protrusion, sometimes referred to herein as a lip 1080. As shown, the lip 1080 can be disposed or segmented across one or more of the arms 1074 and configured to engage an annular groove or recess defined within the throughbore of the metaglene (e.g., catch 324 of FIG. 4C), thereby securing the collet 230 in place at a predetermined depth. In some embodiments, the collet portion 1052 can include a tapered or conical proximal bearing surface 1082 at the proximal end of each arm 1074. As described in more detail below with respect to FIGS. 12A and 12B, the conical or tapered bearing surface 1082 can be used to facilitate removal of the collet.

In some embodiments, the integrated collet/central bone screw 1050 can be laterally or proximally inserted into the central throughbore of the metaglene 1010 and driven into the bony anatomy of the glenoid in as single unitary component. For example, in some embodiments, the integrated collet and central bone screw 1050 can be advanced into the central throughbore of the metaglene (e.g., 310 of FIG. 4C) until the distal tip 1062 of the screw 1050 reaches the threaded distal portion (e.g., 316 of FIG. 4C) of the central throughbore. Once the integrated collet/central bone screw 1050 reaches the threaded distal portion 316, the integrated collet/central bone screw can be screwed loosely through the threaded distal portion to advance the unitary component into bony anatomy of the glenoid.

In some embodiments, as the collet portion 1052 of the unitary component enters the throughbore, the inner sidewall of the throughbore (e.g., 310s of FIG. 4C) bears against the lip 1080 of collet portion 1052 and thereby causes the radially compressible arms 1074 of the collet to flex inward while remaining in contact with the wall. The lip 1080 of the collet portion 1052 can be an annular protrusion disposed across one or more of the arms 1074 and configured to engage an annular groove or catch (e.g., 324 of FIG. 4C) defined horizontally along the inner sidewall 310s of the throughbore 310.

In some embodiments, when the lip 1080 of the collet portion 1052 reaches the location of the catch 324, the radial compression force applied by the inner sidewall 310s can release and cause the collet arms 1074 to flex outward such that the lip snaps into or otherwise mates within the catch. In some embodiments, the engagement of the lip 1080 of the collet portion 1052 and the catch 324 can create an audible and/or tactile cue (e.g., a "click") to notify the surgeon that the collet has reached the desired depth. With the collet portion 1052 secured at the predetermined depth, a glenosphere 1030 or other prosthetic component can be screw or otherwise attached to the metaglene 1010.

Figure 11:
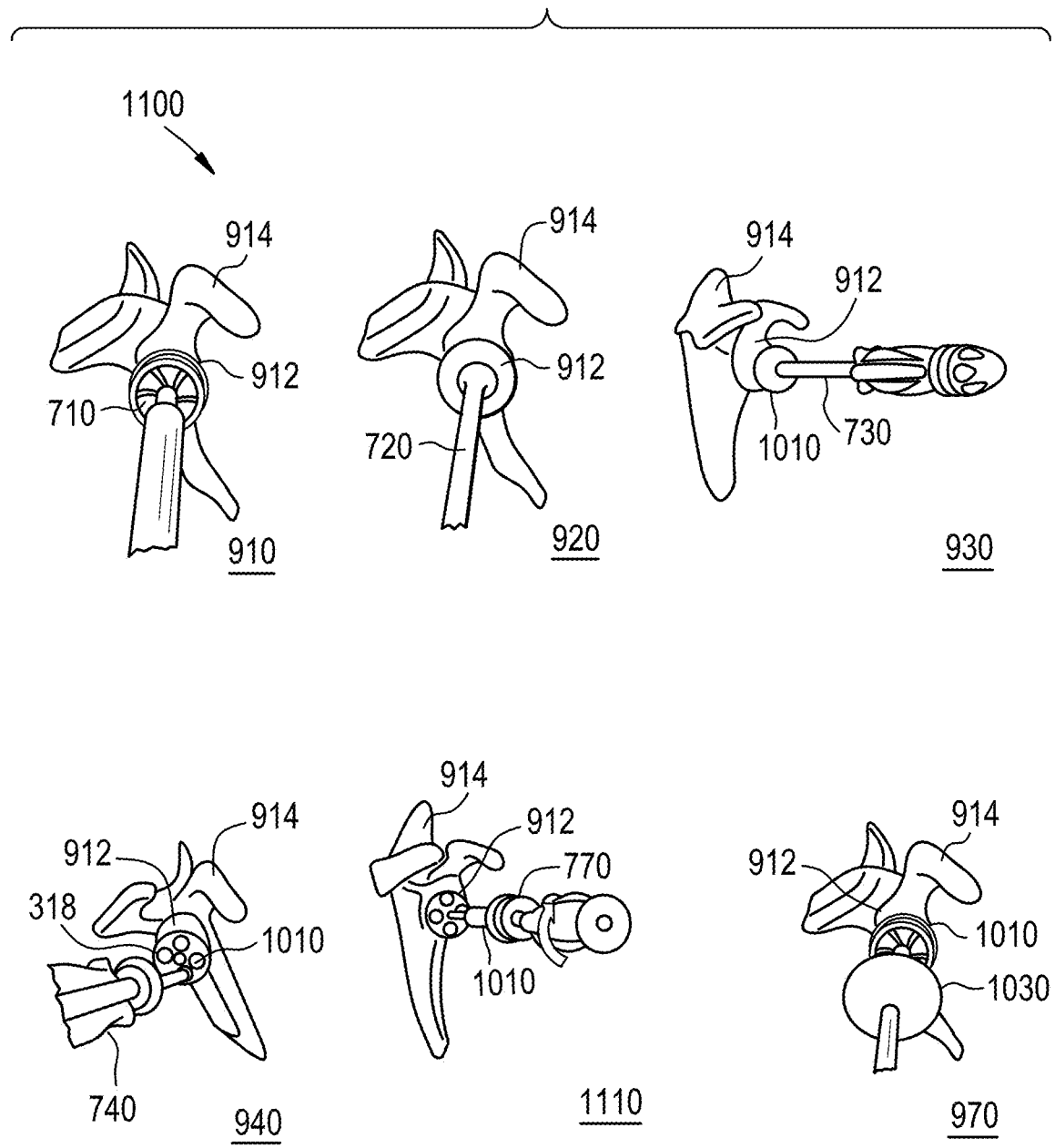
FIG. 11 is a schematic illustration of one exemplary embodiment of a method of implanting a shoulder implant like the shoulder implant of FIGS. 10A-10C.

FIG. 11 illustrates an exemplary embodiment of a method 1100 of implanting the shoulder joint implant 1100 in a patient's scapula. In the illustrated embodiment, the shoulder joint implant 1000 can be implanted as part of a reverse shoulder reconstruction surgery. The method 1100 may include operations in blocks 910, 920, 930, 940, and 970 that are described above with reference to FIG. 9. Accordingly, a detailed description of these operations is omitted here for the sake of brevity.

At block 1110, the integrated collet and central bone screw 1050 (not visible) can be laterally or proximally inserted into the central throughbore defined in the metaglene 1010 through the post and driven into the glenoid through an opening at the distal end of the post of the metaglene 1010. In some embodiments, the integrated collet-bone screw 1050 can be coupled to the distal head of a delivery tool 770. The tool 770 can be operated by the surgeon to push the integrated collet-bone screw 1050 into the central throughbore (e.g., 310, not visible) and then to rotate integrated collet-bone screw 1050 until the bone screw portion 1060 (not visible) is secured to the glenoid 912 as previously described with respect to FIGS. 10A-10C.

Figure 12A:
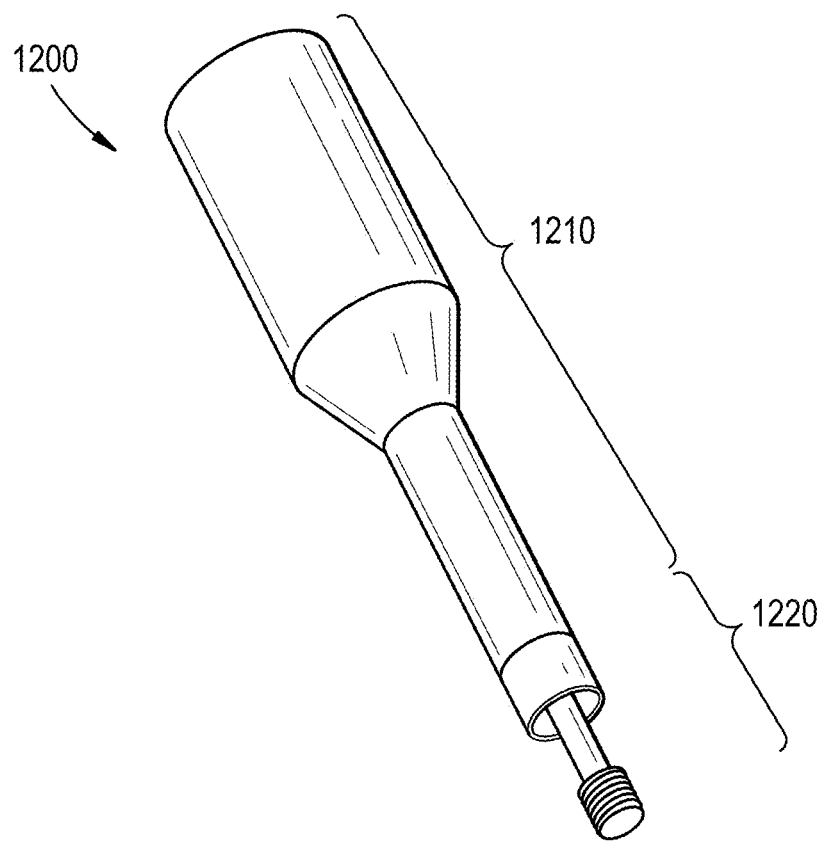
FIG. 12A is a perspective view of one exemplary embodiment of a collet removal tool.
Figure 12B:
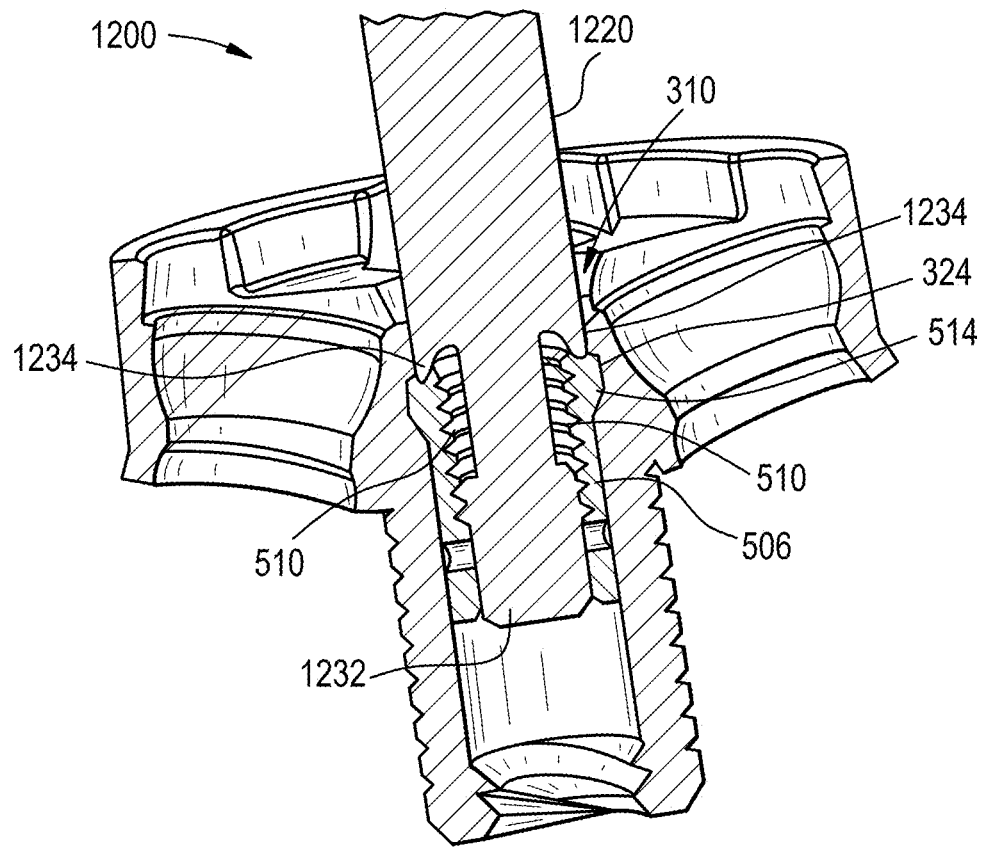
FIG. 12B is a side perspective, cross-sectional view of one exemplary embodiment of the collet removal tool of FIG. 12A being associated with a shoulder joint implant that includes a collet.
Figure 12C:
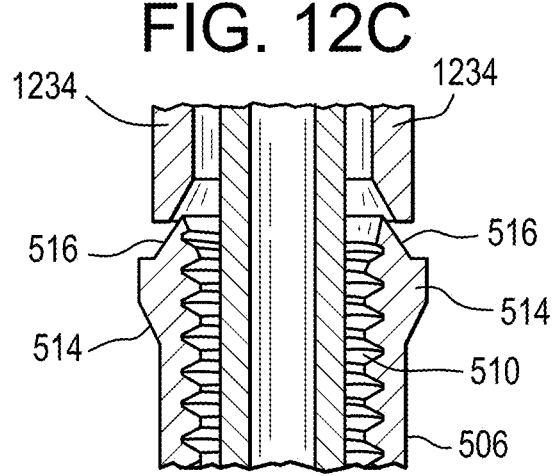
FIG. 12C is a detailed side, partially transparent view of the collet removal tool and collet of FIG. 12B.

FIGS. 12A, 12B, and 12C provide for an exemplary embodiment of a collet removal tool 1200. As shown the collet removal tool 1200 can include a handle portion 1210 and a distal head 1220. For example, in some embodiments, the collet removal tool 1200 can be inserted laterally or proximally into the central throughbore 310 of the metaglene 210. An operator can rotate or otherwise actuate the handle portion 1210 such that the distal head 1220 engages the inner threaded portion 510 of the proximally extending arms 506 of the collet 230.

In some embodiments, the distal head 1220 can include a first engagement mechanism 1232 having a threaded external surface configured to engage the thread portion 510 of the collet 230 as the head is rotated. In some embodiments, the first engagement mechanism 1232 can be a threaded cylindrical body disposed at a distal most end of the head 1220.

As previously discussed with respect to FIG. 4C, a lip 514 of the collet 230 can be secured within a catch 324 or other recessed sidewall portion defined in the throughbore 310. To disengage the lip 514 from the catch 324, the distal head 1220 can include a second engagement mechanism 1234 proximal to the first engagement mechanism 1232. As the head of the tool 1220 is rotated and advanced laterally or proximally, the second engagement mechanism 1234 can be configured to radially compress the arms 506 of the collet 230 radially inward away from the catch 324 in the throughbore.

For example, in some embodiments, the second engagement mechanism 1234 can have a distal-facing bearing service that conforms to the shape or profile at the proximal end of the collet 230. As previously described with respect to FIG. 5, the collet 230 can have a conical or tapered bearing surface 516 at the proximal end of each arm 506 to facilitate removal. Thus, in some embodiments, the second engagement mechanism 1234 can be configured to have a distal-facing bearing surface of the distal head 1220 that complements the collet's conical or tapered bearing surface 516.

As shown in the illustrated embodiment of FIG. 12C, as the operator continues to rotate the handle portion 1210, the head of the tool 1220 can advance laterally or proximally until the distal facing feature surface of the second engagement mechanism 1234 engages the conical or tapered bearing surface 516 of the collet. As the head 1220 further advances, the second engagement mechanism 1234 can radially compress the arms of the collet away from the catch 324 or other recessed sidewall portion and thereby release the lip 514 of collet 230 from the catch. Once the lip 514 of the collet 230 is released from the catch 324, the distal head 1220 can be pulled proximally out of the central throughbore 310 along with the collet which is threadably attached to the first engagement mechanism 1232.

Although the collet removal tool 1200 is described above for removing a collet 230 which is separate from the bone screw 270, one of ordinary skill in the art will recognize that the collet remove tool 1200 can be used to remove an integrated collet/bone screw 1050 from with the central throughbore of a metaglene in a substantially similar manner.

Figure 13A:
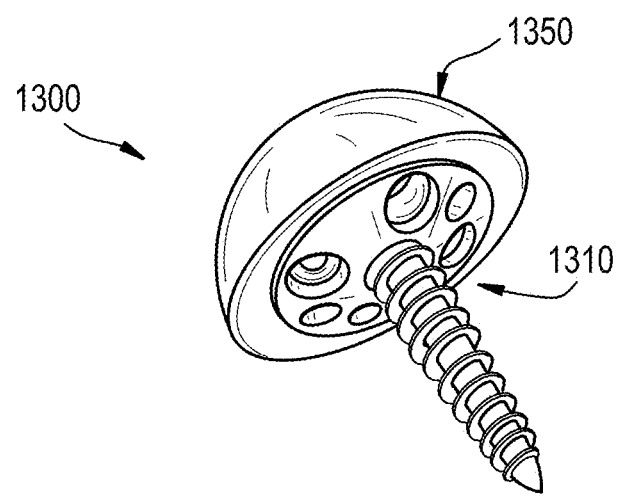
FIG. 13A is a perspective view of yet another exemplary embodiment of a shoulder joint implant.
Figure 13B:
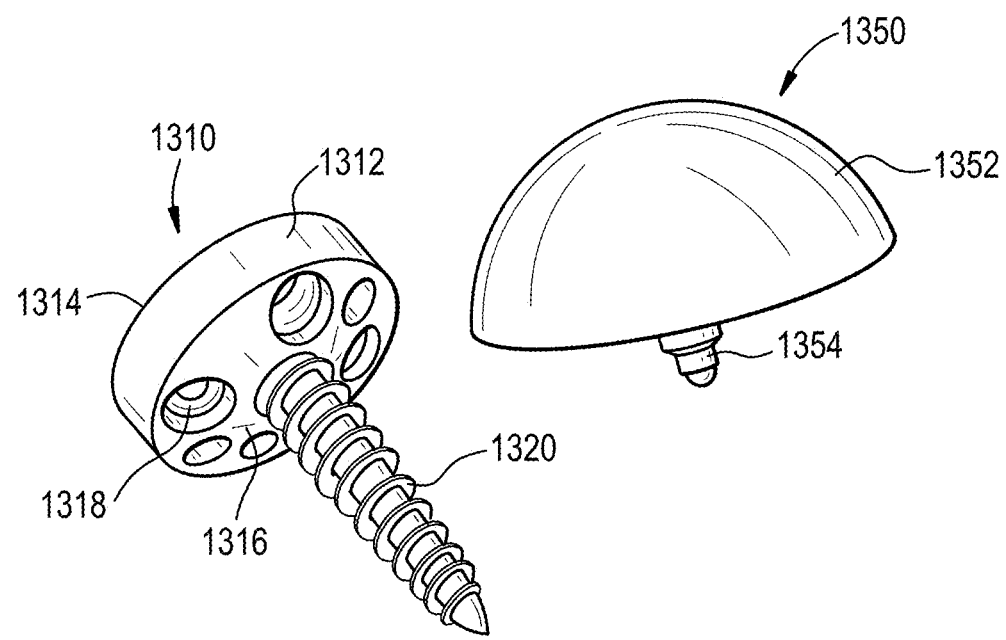
FIG. 13B is a perspective exploded view of components of the shoulder joint implant of FIG. 13A, the components including a metaglene component having an integrated bone screw and a glenosphere component.

FIGS. 13A and 13B are schematic illustrations of an exemplary embodiment of a shoulder joint implant 1300 having a central bone screw integrated into the metaglene. In the illustrated embodiment, the shoulder joint implant 1300 can include a metaglene 1310 and a glenosphere 1350. The metaglene 1310, sometimes referred to herein as a monoblock construct, can include platform 1312 having a proximal-facing surface 1314 and a distal-facing surface 1316. Peripheral bone screws (not shown) can be positioned in some or all of the peripheral screw holes 1318 defined in the platform 1312 and driven into the glenoid to fix the metaglene 1310 in place. In some embodiments, a bone screw portion 1320 can extend outwardly from the distal-facing surface 1316 of the platform 1312 along a central longitudinal axis of the metaglene 1310. As described in more detail with respect to FIG. 15, the bone screw portion 1320 can be screwed into the bony anatomy of the glenoid at the same time that the metaglene 1310 is seated onto the glenoid, and thereby reducing the number of steps needed to install the shoulder joint implant.

In some embodiments, the glenosphere 1350 can include a hemispherical body 1352 having a locking screw 1354 or other coupling element that extends outward from the distal surface 1356 of the hemispherical body 1352. Although the illustrated embodiment disclose fixing a glenosphere 1350 to the metaglene 1310, one of ordinary skill in the art will recognize the other prosthetic components can be coupled to the metaglene, such as but not limited to a glenoid component configured to replace or augment the glenoid surface of the scapula.

Figure 14:
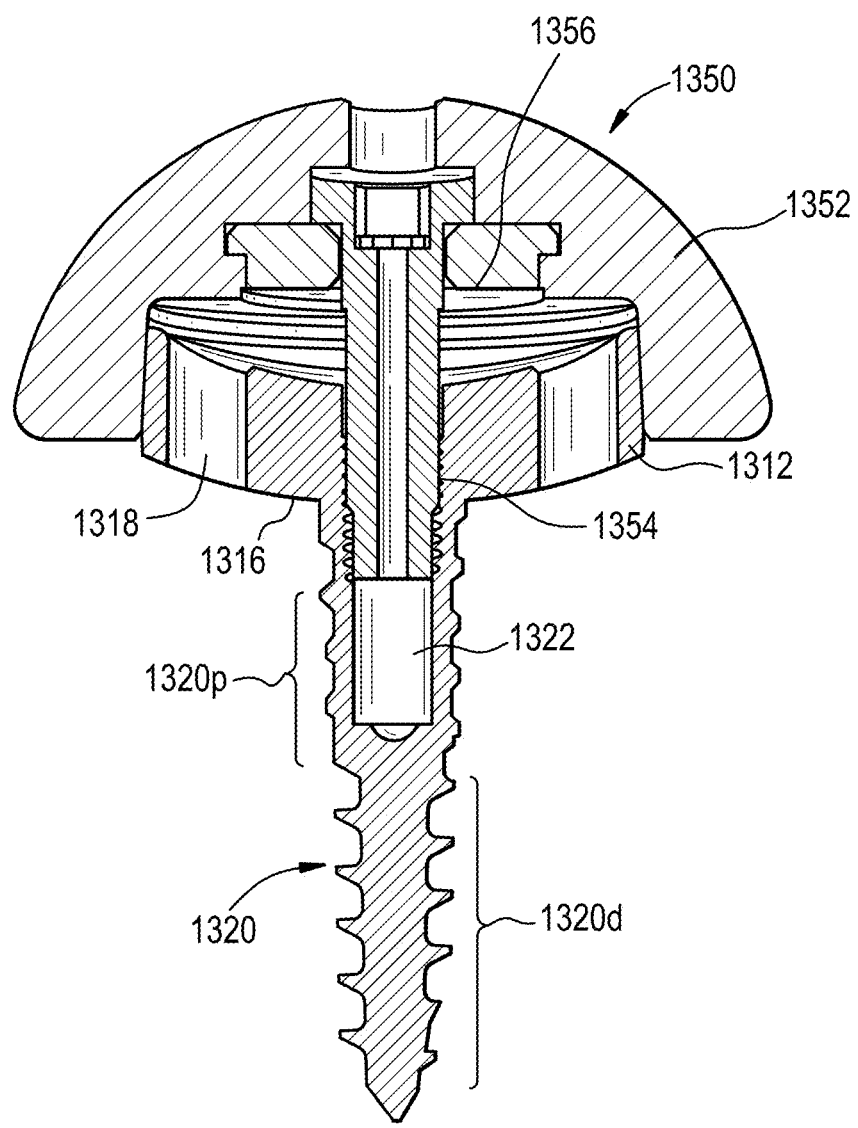
FIG. 14 is a side, partially transparent view of the shoulder joint implant of FIG. 13B.

FIG. 14 is a schematic illustration of a cross section of the metaglene 1310 of FIGS. 13A and 13B having an integrated central bone screw portion 1320. In the illustrated embodiment, the metaglene 1310 includes a central throughbore 1322 configured to extend from the proximal-facing surface 1314 of the platform 1312 and partially into the bone screw portion 1320. The locking screw 1354 of the glenosphere 1350 can be screwed directly into the central throughbore 1322 to draw the distal-facing surface 1356 of the glenosphere body 1352 onto the proximal-facing surface 1314 of the metaglene platform 1312. In some embodiments, a proximal end of the central throughbore 1322$p$ can be configured to threadably engage central locking screw 1354 of the glenosphere 1350. As shown in the illustrated embodiment, the outer thread diameter of the bone screw portion 1320 can be greater at a proximal end portion 1320$p$ than the outer thread diameter at a distal end portion 1320$d$ in order to accommodate to the diameter of the locking screw 1354.

Figure 15:
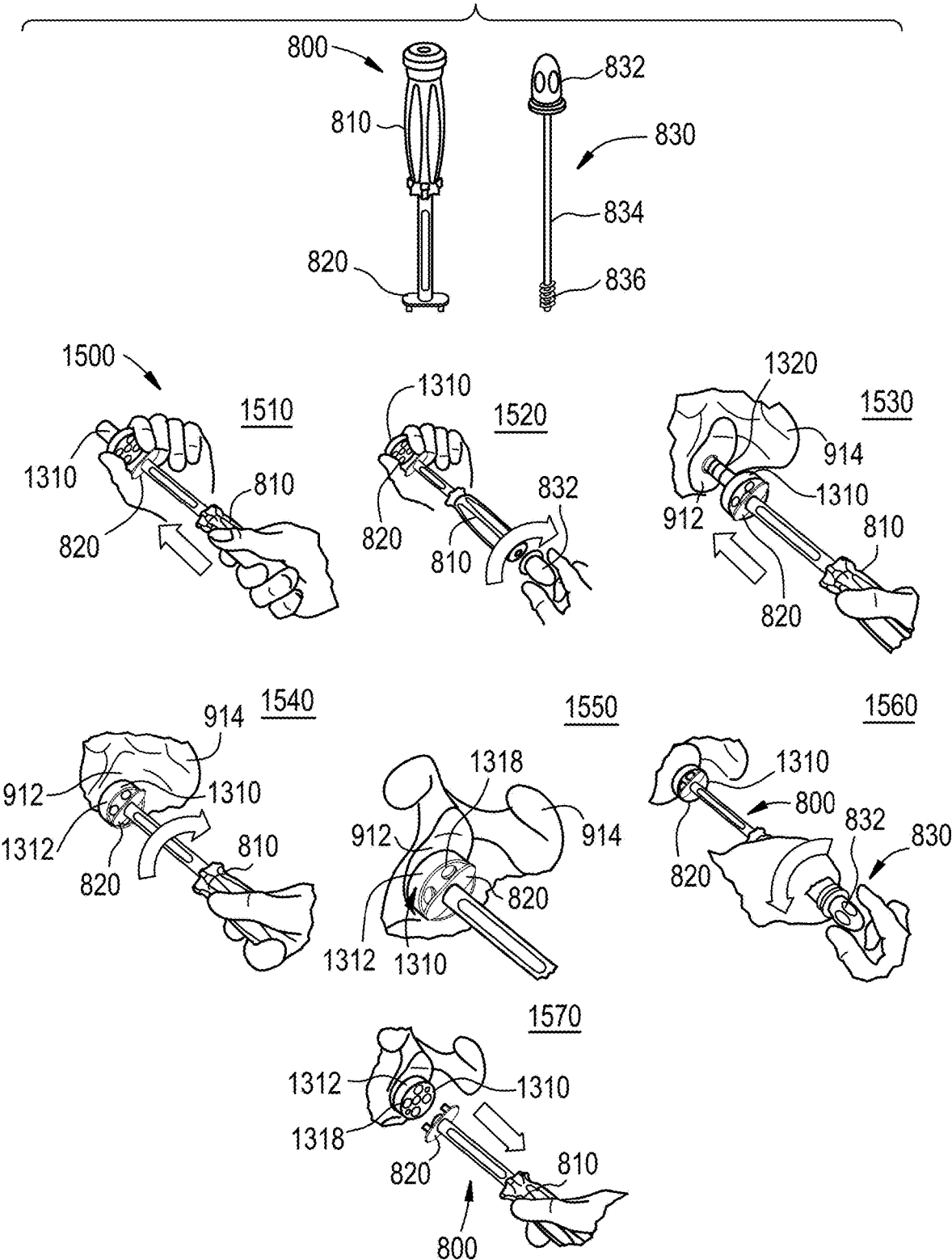
FIG. 15 is a schematic illustration of one exemplary embodiment of a method of implanting a shoulder joint implant like the shoulder implant of FIGS. 13A and 13B.

FIG. 15 illustrates an exemplary embodiment of a method 1500 for implanting the shoulder joint implant 1300 of FIGS. 13A and 13B into a patient's scapula. In the illustrated embodiment, the shoulder joint implant 1300 can be implanted as part of a reverse shoulder reconstruction surgery.

At block 1510, the metaglene 1310 having an integrated central bone screw portion, or monoblock construct, can be attached to a distal end of a monoblock delivery instrument 800. In some embodiments, the monoblock delivery instrument 800 can have a handle portion 810, a distal head 820, and a locking mechanism 830. The distal head 820 can be specifically adapted to engage one or more of the screw holes 1318 or other locking feature defined on the proximal face 1314 of the platform 1312.

At block 1520, the monoblock construct 1310 can be locked to the monoblock delivery instrument 800 using the locking mechanism 830. In some embodiments, the locking mechanism 830 can include a handle portion 832 and an elongated shaft 834 having a distal threaded head 834. The locking mechanism 830 can be laterally or proximally inserted through a cannula defined along a central axis of the handle portion 810 and the distal head 820 and received within the central throughbore 1322 (not visible) of the monoblock construct 1310. The handle portion 832 of the locking mechanism 830 can be rotated in a direction (e.g., clockwise) such that the threaded head 836 of the locking mechanism 830 threadably engages the central throughbore and thereby locks the monoblock construct 1310 to the distal head 820 of the monoblock delivery instrument 800.

At block 1530, the monoblock construct 1310 can be inserted into a hole drilled into the glenoid 912 of a patient's scapula 914. For example, as shown in the illustrated embodiment, the monoblock delivery instrument 800 can push the bone screw portion 1320 extending from the monoblock construct 1310 into the hole.

At block 1540, the monoblock construct 1310 can be seated onto the glenoid 912, such that the bone screw portion 1320 (not visible) is screwed into the glenoid vault (not visible) and the distal-facing surface 1316 (not visible) of the metaglene platform 1312 is seated on the bony surface of the glenoid 912. As shown in the illustrated embodiment, the monoblock delivery instrument 800 can be rotated in a tightening direction (e.g., clockwise) to screw the bone screw portion 1320 until a distal-facing surface 1316 (not visible) of the monoblock construct 1310 is seated onto the glenoid.

At block 1550, the peripheral screw holes 1318 of the platform 1312 of the monoblock construct 1310 can be aligned. In some embodiments, the handle portion 810 of the monoblock delivery instrument 800 can be rotated as needed in a clockwise and/or a counter clockwise direction to align the peripheral screw holes 1318 such that peripheral screws (not shown) can be inserted and driven through the screw holes in one or more of a superior, inferior, medial and/or lateral position with respect to the surface of the glenoid bone.

At block 1560, the handle portion 832 of the locking mechanism 830 can be rotated in a direction to unlock the monoblock construct 1310 from the distal head 820 of the monoblock delivery instrument 800. For example, as shown in the illustrated embodiment, the handle portion 832 of the locking mechanism 830 can be rotated counter-clockwise to disengage the threaded head 836 (not visible) of the locking mechanism 830 from the central throughbore (e.g., 1322, not visible) of the monoblock construct 1310 and thereby unlock the monoblock construct 1310 from the distal head 820 of the monoblock delivery instrument 800.

At block 1570, the monoblock delivery instrument 800 can be removed from the monoblock construct 1310 by proximally pulling the instrument away from the construct. After the monoblock inserter instrument is removed, peripheral screws can be inserted and driven through the peripheral screw holes 1318 in the platform 1312 of the monoblock construct 1310. Alternatively or additionally, the glenosphere 1350 (not shown) can be secured to the platform 1312 of the monoblock construct 1310 by screwing the locking screw 1354 (not shown) into the threaded portion of the central throughbore 1322 (not shown).

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein. All publications and references cited herein are expressly incorporated herein by reference in their entirety.

What is claimed is:

1. A shoulder joint implant, comprising:
   a first prosthetic component that includes a coupling element protruding from a distal bearing surface thereof;
   a baseplate configured to secure the first prosthetic component to bone, the baseplate including a post protruding from a distal bearing surface thereof and defining a throughbore that extends along a proximal-distal axis of the post; and
   a removable bone screw that includes a collet portion disposed at a proximal end thereof and a threaded portion at a distal end thereof,
   the collet portion disposed within the throughbore and configured to engage the coupling element of the first prosthetic component such that the first prosthetic component is fixedly coupled to the baseplate.

2. The implant of claim 1, wherein the collet portion of the removable bone screw is dimensioned to engage the coupling element, the coupling element having a diameter that is less than a diameter of the throughbore of the baseplate.

3. The implant of claim 1, wherein a plurality of screw holes are defined in the baseplate adjacent the throughbore and the implant further comprises a plurality of peripheral bone screws disposed through the plurality of screw holes and configured to secure the baseplate implant to bone.

4. The implant of claim 1, wherein the collet portion of the removable bone screw comprises a plurality of proximally-extending arms that are radially compressible to facilitate at least one of insertion and removal of the collet in the throughbore of the baseplate.

5. The implant of claim 4, wherein one or more of the plurality of arms comprise a lateral protrusion configured to engage an annular recessed portion of an inner sidewall of the throughbore when the arms are not compressed, thereby fixing the collet portion of the removable bone screw at a predetermined depth in the throughbore of the baseplate.

6. The implant of claim 4, wherein the collet portion of the removable bone screw includes one or more keys protruding from one or more of the arms of the collet, the one or more keys being configured to engage with one or more keyways defined longitudinally along an inner sidewall of the throughbore of the baseplate to align and guide the removable bone screw into the baseplate.

7. The implant of claim 6, wherein the one or more keys are configured to engage with the one or more keyways defined along the inner sidewall of the throughbore to resist rotation of the collet portion of the removable bone screw while disposed within the throughbore of the baseplate.

8. The implant of claim 6, wherein the one or more keys of the collet portion are configured to engage with the one or more keyways along the inner sidewall of the throughbore to form a locking mechanism that provides a torsional resistive force that counteracts a torque imparted by the coupling element of the first prosthetic component while screwing the coupling element of the first prosthetic component into the collet portion of the removable bone screw to form a taper lock between the first prosthetic component and the baseplate or while unscrewing the coupling element out of the collet portion to break the taper lock between the first prosthetic component and the baseplate.

9. The implant of claim 6, wherein the length of the one or more keyways define a distal most depth at which the collet portion of the removable bone screw is seated in the throughbore of the baseplate.

10. The implant of claim 9, wherein an annular recessed portion is defined in the inner sidewall of the throughbore and configured to capture a lateral protrusion from one or more of the plurality of arms of the collet portion when inserted into the throughbore,
wherein the distance between the annular recessed portion and the distal most depth of the one or more keyways is a predefined distance that is greater than the height of the collet portion such that the collet portion bottoms out at the distal end of the one or more keyways when the coupling element of the glenosphere component is unscrewed from the collet.

11. The implant of claim 4, wherein the one or more compressible arms of the collet portion have a proximal ramped bearing surface configured to bear against a counterpart bearing surface of a prosthetic implant tool, the one or more compressive arms being radially compressed in response to the counterpart bearing surface of the prosthetic implant tool bearing against the proximal ramped bearing surface, thereby disengaging the lateral protrusion of the one or more compressible arms from the recessed portion of the inner sidewall of the throughbore.

12. The implant of claim 1, wherein the first prosthetic component is a glenosphere component having an integrated locking screw protruding from a distal bearing surface thereof.

13. A method of implanting a shoulder prosthetic implant in a scapula of a patient, comprising:
reaming a glenoid of a scapula such that a surface of the glenoid is complementary to a distal bearing surface of a baseplate of a prosthetic shoulder implant;
drilling a hole into the glenoid to receive a post that protrudes from the distal bearing surface of the baseplate;
disposing the post of the baseplate into the glenoid through the drilled hole;
securing a plurality of peripheral bone screws into the glenoid through one or more screw holes defined in the baseplate;
laterally inserting a removable collet into a throughbore defined in the baseplate, wherein the throughbore extends along a proximal-distal axis of the baseplate of the post; and
securing a first prosthetic component of the prosthetic shoulder implant onto a proximal bearing surface of the baseplate such that a coupling element protruding from a distal bearing surface of the first prosthetic component is secured to the collet within the throughbore of the baseplate.

14. The method of claim 13, wherein the collet is coupled to a proximal head of a central bone screw and the method further comprises:
laterally inserting a central bone screw through the throughbore of the baseplate prior to inserting the removable collet; and
securing a distal threaded portion of the central bone screw into the glenoid through an opening at the distal end of the post of the baseplate.

15. The method of claim 13, wherein the collet is coupled to a proximal head of a central bone screw and the method further comprises:
laterally inserting the collet and the central bone screw together into the throughbore of the baseplate; and
securing a distal threaded portion of the central bone screw into the glenoid through an opening at the distal end of the post of the baseplate.

16. The method of claim 13, wherein the throughbore of the baseplate is dimensioned to facilitate insertion of a central bone screw having a diameter that is greater than a diameter of the coupling element of the first prosthetic component.

17. The method of claim 16, wherein the collet is dimensioned to engage the coupling element of the first prosthetic component having a diameter that is less than a diameter of the central bone screw.

18. The method of claim 13, wherein the first prosthetic component is a glenosphere component having an integrated locking screw protruding from a distal bearing surface thereof.

19. The implant of claim 1, wherein the removable bone screw further comprises a shoulder portion, the shoulder portion including a conical bearing surface that extends inward at an oblique angle between the collet portion and threaded portion.

20. The implant of claim 19, wherein the removable bone screw further comprises a neck portion, the neck portion being disposed between the shoulder portion and the threaded portion.

21. The implant of claim 19, wherein the throughbore comprises threads disposed on the inner surface of the distal portion, the threads being configured at an oblique angle to serve as a proximal bearing surface for the conical bearing surface of the removable bone screw.

22. A method of implanting a shoulder prosthetic implant in a scapula of a patient, comprising:
reaming a glenoid of a scapula such that a surface of the glenoid is complementary to a distal bearing surface of a baseplate of a prosthetic shoulder implant;
drilling a hole into the glenoid to receive a post that protrudes from the distal bearing surface of the baseplate;
disposing the post of the baseplate into the glenoid through the drilled hole;
securing a plurality of peripheral bone screws into the glenoid through one or more screw holes defined in the baseplate;
laterally inserting a removable bone screw into a throughbore defined in the baseplate such that a collet portion of the bone screw is seated within the throughbore, wherein the throughbore extends along a proximal-distal axis of the baseplate of the post;
securing a distal threaded portion of the bone screw into the glenoid through an opening at a distal end of the post of the baseplate; and
securing a first prosthetic component of the prosthetic shoulder implant onto a proximal bearing surface of the baseplate such that a coupling element protruding from a distal bearing surface of the first prosthetic component is secured to the collet within the throughbore of the baseplate.

23. The method of claim 22, wherein the bone screw includes a shoulder portion that extends inward at an oblique angle between the collet portion and a distal threaded portion, the shoulder portion serving as a distal bearing surface when the bone screw is inserted through the throughbore.

* * * * *